United States Patent
Hedenstrom et al.

(10) Patent No.: US 6,706,728 B2
(45) Date of Patent: Mar. 16, 2004

(54) SYSTEMS AND METHODS FOR TREATING A MUCOSAL SURFACE

(75) Inventors: John C. Hedenstrom, St. Paul, MN (US); Michael J. Jozwiakowski, Stillwater, MN (US); Mark Martinez, San Franciso, CA (US); Kenneth R. Phares, Chapel Hill, NC (US); Kenneth Trofatter, Jr., Minnetonka, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/238,662

(22) Filed: Sep. 10, 2002

(65) Prior Publication Data

US 2003/0045543 A1 Mar. 6, 2003

Related U.S. Application Data

(63) Continuation of application No. 09/886,012, filed on Jun. 22, 2001, now abandoned, which is a continuation-in-part of application No. 09/676,339, filed on Sep. 29, 2000, now Pat. No. 6,486,168, which is a continuation of application No. 09/479,578, filed on Jan. 7, 2000, now Pat. No. 6,245,776.

(60) Provisional application No. 60/213,420, filed on Jun. 22, 2000, and provisional application No. 60/115,253, filed on Jan. 8, 1999.

(51) Int. Cl.$^7$ .............................................. A61K 31/44
(52) U.S. Cl. ...................... 514/293; 514/292; 514/303
(58) Field of Search ............................... 514/293, 292, 514/303

(56) References Cited

U.S. PATENT DOCUMENTS

| | | | |
|---|---|---|---|
| 545,102 A | 8/1895 | Sleem | |
| 652,848 A | 7/1900 | Hill | |
| 1,711,341 A | 4/1929 | Cook | |
| 1,794,221 A | 2/1931 | Washburn et al. | |
| 2,518,486 A | 8/1950 | Mende | |
| 2,616,423 A | 11/1952 | Kurkjian | |
| 2,705,496 A | 4/1955 | Svenson | |

(List continued on next page.)

FOREIGN PATENT DOCUMENTS

| | | |
|---|---|---|
| EP | 0 894 797 A1 | 2/1998 |
| JP | 9-208584 | 8/1997 |
| WO | 93/09119 | 5/1993 |
| WO | 97/41884 | 11/1997 |
| WO | 97/48704 | 12/1997 |
| WO | 98/24436 | 6/1998 |
| WO | 99/29693 | 6/1999 |
| WO | 00/06577 | 2/2000 |
| WO | 00/09506 | 2/2000 |
| WO | 00/40228 | 7/2000 |
| WO | 00/76505 | 12/2000 |
| WO | 00/76518 | 12/2000 |
| WO | 00/76519 | 12/2000 |

OTHER PUBLICATIONS

Miller, R.L., et al., Imiquimod applied topically: a novel immune response modifier and new class of drug, international Journal of Immunopharmacology, Vol 21, 1999, pps. 1–14.

R. Snoeck, G. Andrei and E. De Clercq, "Specific Therapies for Human Papilloma Virus Infections", Current Opinion in Infectious Diseases, 1998, vol. 11, pp. 733–737.

"3M Pharmaceuticals unveils research and development and expansion plans" retrieved from STN International, No. 2138, p. 10–. . . (1996).

Harrison, C.J. et al., "Effects of Cytokines and R–837 a Cytokine Inducer on UV–Irradiation Augmented Recurrent Genital Herpes in Guinea–Pigs", Antiviral Research, 1991, vol. 15, No. 4, pp. 315–322.

Harrison C.J. et al., "Modification of Immunological Responses and Clinical Disease During Topical R–837 treatment of Genital HSV–2Infection", Antiviral Research, 1989, vol. 10, No. 4–5, pp. 209–224.

Chollet, J.L. et al., "Development of a Topically Active Imiquimod Formulation", Pharmaceutical Development and Technology, New York, NY, US Jan. 1999, vol. 4, No. 1, pp. 35–43.

Dittgen, M. et al., Acrylic Polymers. A review of Pharmaceutical Applications, STP Pharma Pratiques, Paris, FR, (1997) vol. 7, No. 6, pp. 403–437.

Wozniak, et al., The Amination of 3–nitro–1, 5–naphthyridines by Liquid Ammonia/Potassium Chemical Society, 102, pp. 511–513, Dec. 12, 1983.

Brennan, et al., "Automated Bioassay of Interferons in Micro–test Plates", Biotechniques, Jun./Jul., 78,1983.

Testerman, et al., "Cytokine Inudction by the Immunomodulators Imiquimod and S–27609", Journal of Leukocyte Biology, vol. 58, pp. 365–372, Sep. 1995.

Bachman, et al., "Synthesis of Substituted Quninolylamines. Derivatives of 4–Amino–7–Chloroquinoline", J. Org. Chem., 15 pp. 1278–1284 (1950).

Jain, et al., "Chemical and Pharmacological Investigations of Some ω–Substituted Alkylamino–3–aminopyridines", J. Med. Chem., 11 pp. 87–92 (1968).

Baranov, et al., Chem. Abs. 85, 94371, (1976).

Berenyi, et al., "Ring Transformation of Condensed Dihydro–as–triazines", J. Heterocyclic Chem., 18, pp. 1537–1540 (1981).

Buck, et al; "Successful Treatment of Vaginal Intraepithelial Neoplasia with Imiquimod 5% Cream" (unpublished manuscript being submitted for publication), no date available.

*Primary Examiner*—Raymond Henley, III
(74) *Attorney, Agent, or Firm*—Ted Ringsred

(57) ABSTRACT

A system for treating a condition associated with a mucosal surface, the system comprising an immune response modifier (IRM) compound chosen from imidazoquinoline amines, imidazopyridine amines, 6,7-fused cycloalkylimidazopyridine amines, imidazonaphthyridine amines, oxazoloquinoline amines, thiazoloquinoline amines, 1,2-bridged imidazoquinoline amines, and pharmaceutically acceptable salts thereof and an applicator device for applying the IRM compound to the mucosal surface. This system of IRM compounds and applicator may be used to treat conditions associated with mucosal surfaces such as cervical dysphasia and cervical intraepithelial neoplasia.

39 Claims, 12 Drawing Sheets

U.S. PATENT DOCUMENTS

| | | |
|---|---|---|
| 2,826,198 A | 3/1958 | Sickle |
| 3,220,413 A | 11/1965 | Sunnen |
| 3,314,941 A | 4/1967 | Littell et al. |
| 3,424,158 A | 1/1969 | Silver |
| 3,506,008 A | 4/1970 | Huck |
| 3,823,715 A | 7/1974 | Holanek et al. |
| 3,917,624 A | 11/1975 | El-Haj et al. |
| 4,137,922 A | 2/1979 | Leininger et al. |
| 4,689,338 A | 8/1987 | Gerster |
| 4,698,348 A | 10/1987 | Gerster |
| 4,826,830 A | 5/1989 | Han et al. |
| 4,858,624 A | 8/1989 | Shihata |
| 4,900,315 A | 2/1990 | Lundqvist et al. |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster et al. |
| 5,268,376 A | 12/1993 | Gester |
| 5,282,789 A | 2/1994 | Lundy |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,397,312 A | 3/1995 | Rademaker et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,531,703 A | 7/1996 | Skwarek et al. |
| 5,585,612 A | 12/1996 | Harp, Jr. |
| 5,605,899 A | 2/1997 | Gerster et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,741,908 A | 4/1998 | Gerster et al. |
| 5,741,909 A | 4/1998 | Gerster et al. |
| 5,773,413 A | 6/1998 | Jaynes et al. |
| 5,782,801 A | 7/1998 | Caillouette |
| 5,886,006 A | 3/1999 | Nikolaides et al. |
| 5,939,090 A | 8/1999 | Beaurline et al. |
| 5,977,366 A | 11/1999 | Gerster et al. |
| 6,069,149 A | 5/2000 | Nanba et al. |
| 6,110,929 A | 8/2000 | Gerster et al. |
| 6,245,776 B1 | 6/2001 | Skwierczynski et al. |

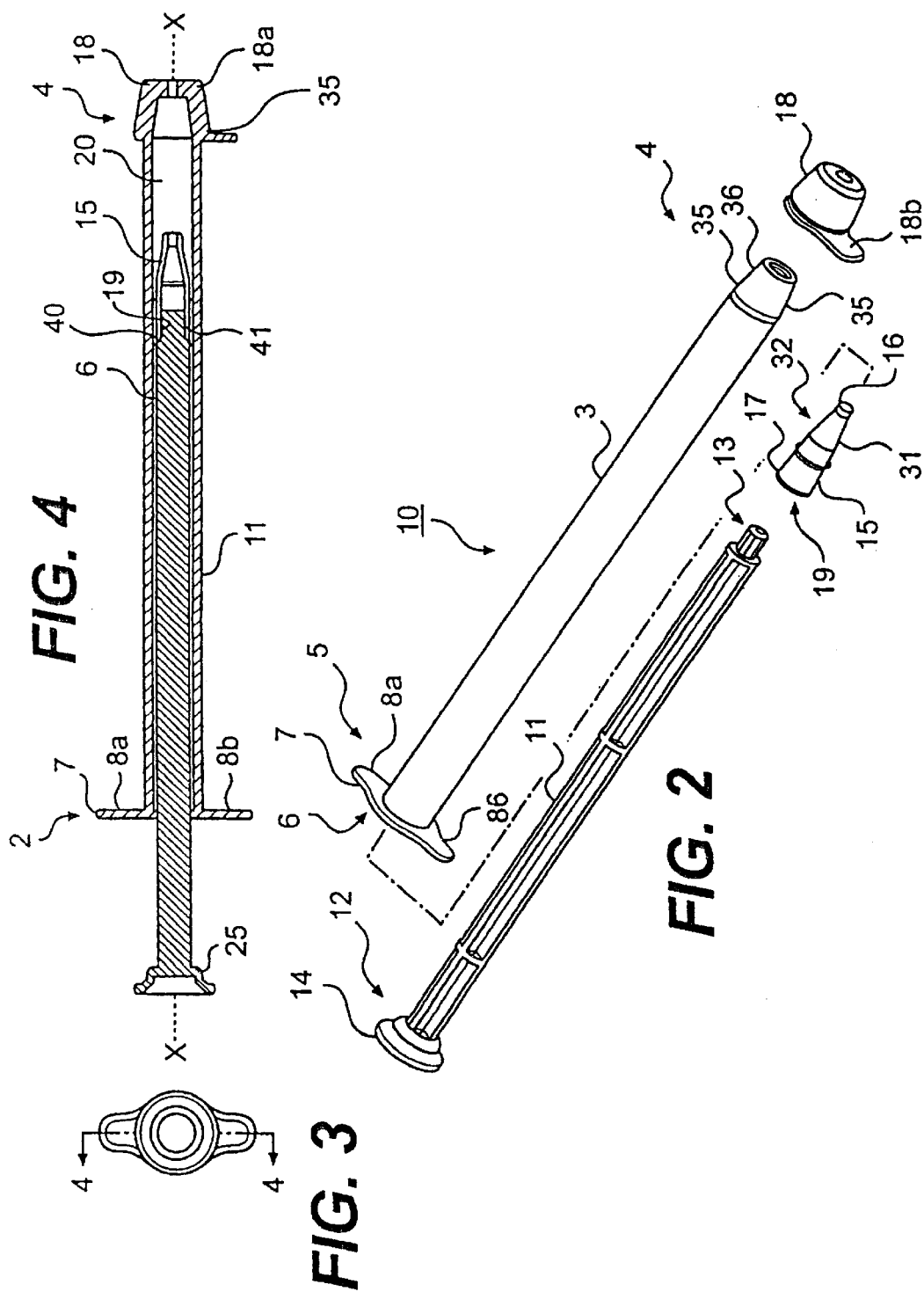

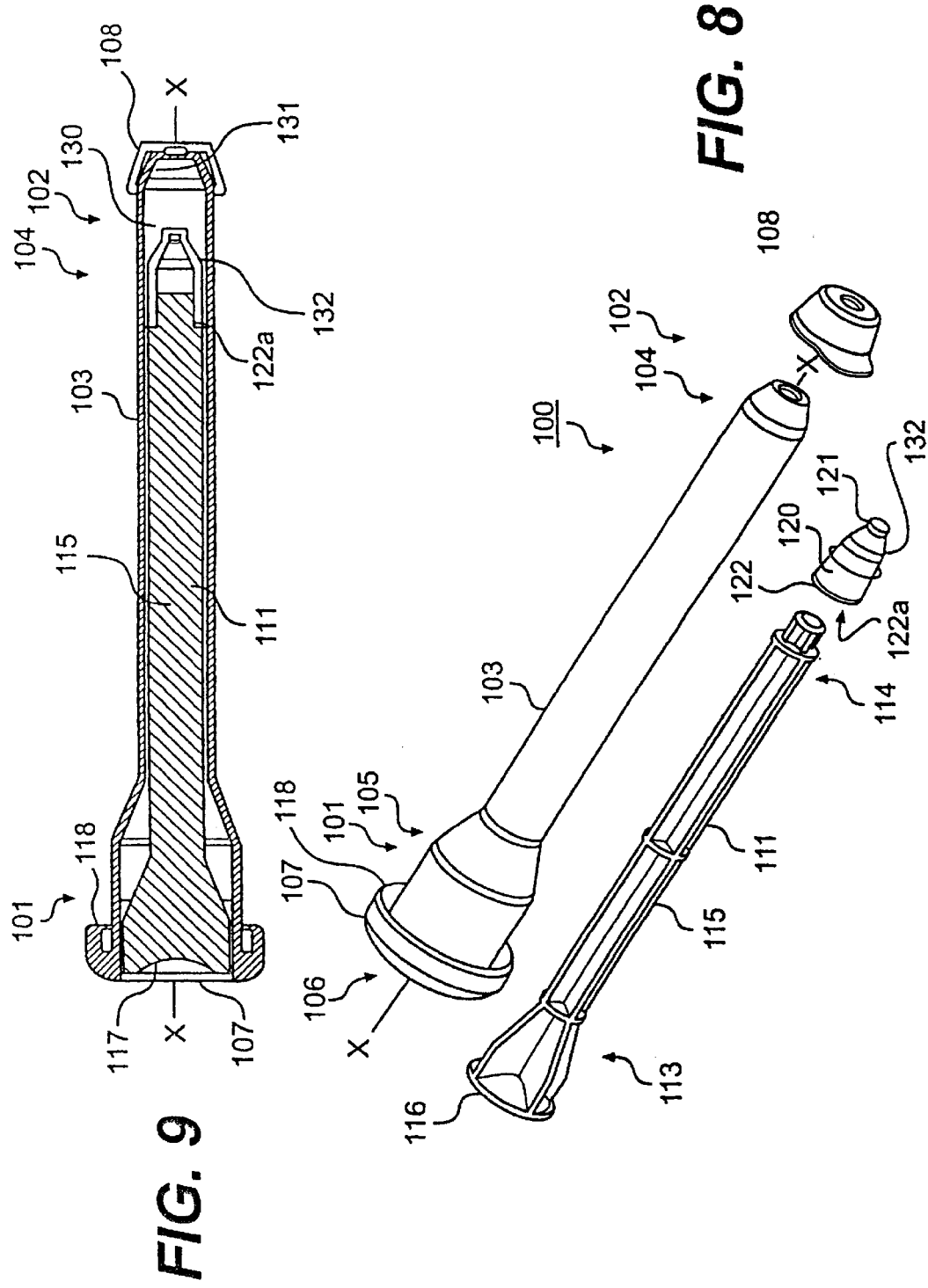

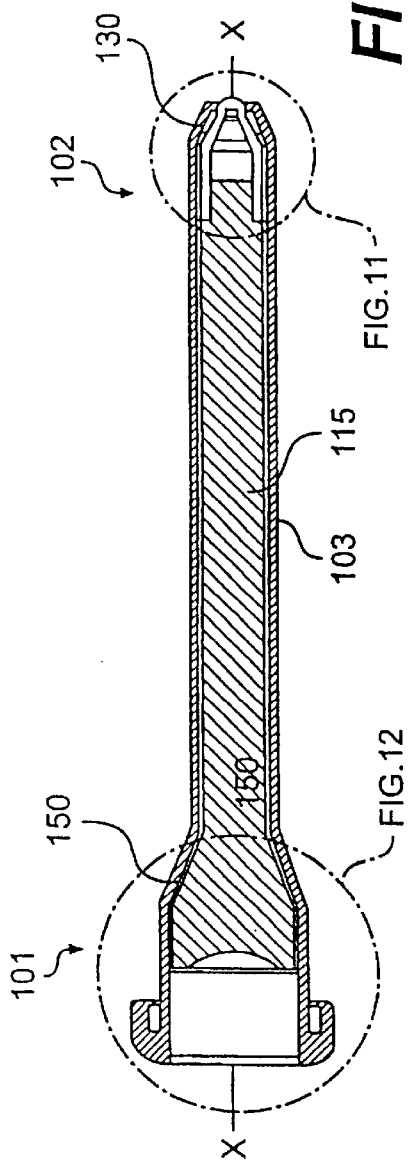
FIG. 10
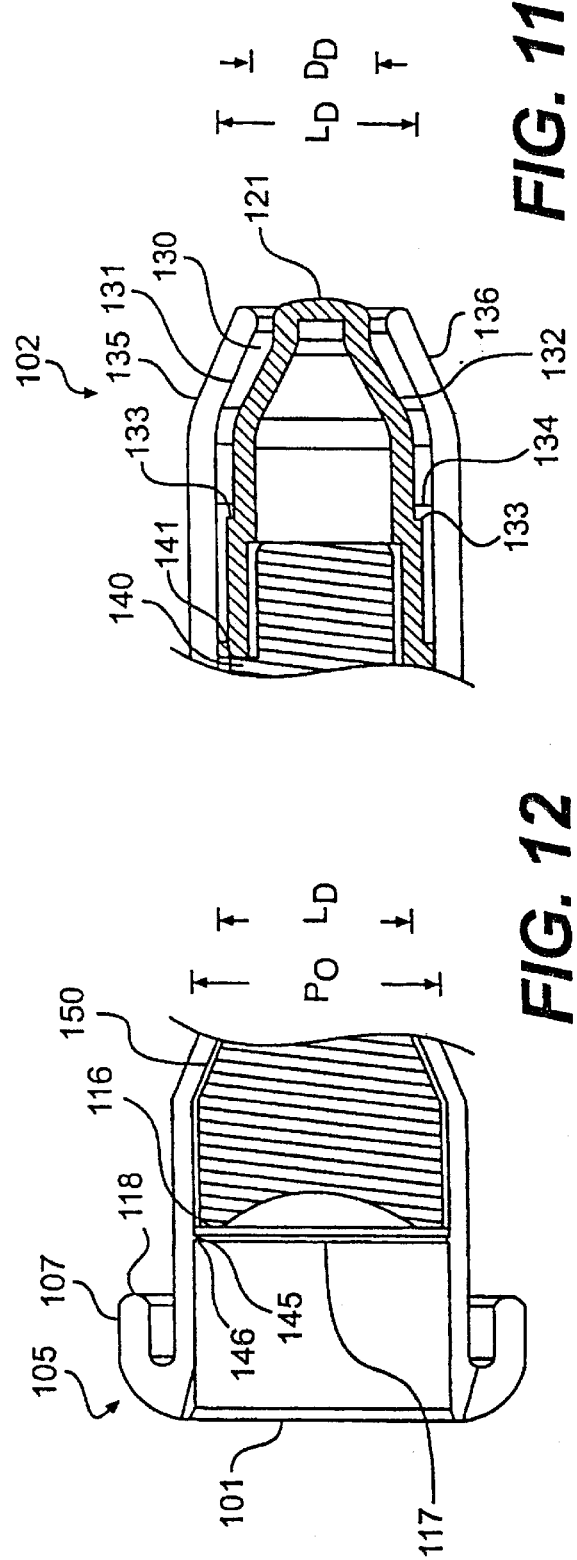
FIG. 11
FIG. 12

SYSTEMS AND METHODS FOR TREATING A MUCOSAL SURFACE

This application is a continuation of U.S. application Ser. No. 09/886,012, filed Jun. 22, 2001, now abandoned, which claims benefit of Provisional Application No. 60/213,420, filed Jun. 22, 2000, and which is a continuation-in-part of U.S. application Ser. No. 09/676,339, filed Sep. 29, 2000, now U.S. Pat. No. 6,486,168, which is a continuation of application No. 09/479,578, filed Jan. 7, 2000, now U.S. Pat. No. 6,245,776, which claims priority to provisional application No. 60/115,253, filed Jan. 8, 1999. In addition, the disclosure of each of the above-mentioned applications is incorporated herein by reference.

DESCRIPTION OF THE INVENTION

1. Field of the Invention

The present invention relates to systems and methods for treating a condition associated with a mucosal surface, such as the vaginal part of the cervix. In particular, the systems and methods may involve an immune response modifier (IRM) compound chosen from imidazoquinoline amines, imidazopyridine amines, 6,7-fused cycloalkylimidazopyridine amines, imidazonaphthyridine amines, oxazoloquinoline amines, thiazoloquinoline amines, 1,2-bridged imidazoquinoline amines, and pharmaceutically acceptable salts thereof. In one optional embodiment, the invention provides systems and methods which are particularly advantageous for topical application to the cervix for treatment of cervical conditions such as cervical dysplasias including dysplasia associated with human papillomavirus (HPV).

The present invention is also directed to medicament delivery arrangements and methods of use. Some aspects of the invention are directed to the delivery of a pharmacological agent to a selected location with minimal delivery to regions surrounding the selected location. In some optional embodiments the invention is particularly advantageous for topical delivery of a pharmacological agent to the uterine cervix.

2. Background of the Invention

Many imidazoquinoline amine, imidazopyridine amine, 6,7-fused cycloalkylimidazopyridine amine, 1,2-bridged imidazoquinoline amine, thiazolo- and oxazoloquinolinamines and pyridinamines, imidazonaphthyridine and tetrahydroimidazonaphthyridine amine compounds have demonstrated potent immunostimulating, antiviral and antitumor (including anticancer) activity, and have also been shown to be useful as vaccine adjuvants to enhance the protective immune system response to vaccines. These compounds are hereinafter sometimes collectively referred to as the "IRM" (immune response modifier) compounds of the invention. An IRM compound may be selected from the group comprising imidazoquinoline amines, imidazopyridine amines, 6,7-fused cycloalkylimidazopyridine amines, imidazonaphthyridine amines, oxazoloquinoline amines, thiazoloquinoline amines 1,2-bridged imidazoquinoline amines, and pharmaceutically acceptable salts thereof. Methods for preparing such IRMs and pharmaceutical compositions containing them are disclosed in, for example, U.S. Pat. Nos. 4,689,338; 5,389,640; 5,268,376; 4,929,624; 5,266,575; 5,352,784; 5,494,916; 5,482,936; 5,346,905; 5,395,937; 5,238,944; 5,525,612; 5,175,296; 5,693,811; 5,741,908; 5,939,090; 6,110,929; 4,988,815; 5,376,076; and PCT Publications WO 99/29693; WO 00/76505; WO 00/76518; and WO 00/76519. The entire disclosure of each of these patents and patent applications is incorporated herein by reference.

The immunostimulating, antiviral and antitumor activities of these compounds have been discussed in detail, and certain specific diseases have been identified as being susceptible to treatment therewith, including basal cell carcinoma, eczema, essential thrombocythaemia, hepatitis B, multiple sclerosis, neoplastic diseases, psoriasis, rheumatoid arthritis, type I herpes simplex, type II herpes simplex, and warts. One of these IRM compounds, known as imiquimod, has been commercialized in a topical formulation, Aldara™, for the treatment of anogenital warts associated with human papillomavirus.

The mechanism for the antiviral and antitumor activity of these IRM compounds is thought to be due in substantial part to enhancement of the immune response due to induction of various important cytokines (e.g., interferons, interleukins, tumor necrosis factor, etc.). Such compounds have been shown to stimulate a rapid release of certain monocyte/macrophage-derived cytokines and are also capable of stimulating B cells to secrete antibodies which play an important role in these IRM compounds' antiviral and antitumor activities. One of the predominant immunostimulating responses to these compounds is the induction of interferon (IFN)-α production, which is believed to be very important in the acute antiviral and antitumor activities seen. Moreover, up regulation of cytokines such as, for example, tumor necrosis factor (TNF), IL-1 and IL-6 also have potentially beneficial activities and are believed to contribute to the antiviral and antitumor properties of these compounds.

Although some of the beneficial effects of IRMs are known, the ability to provide therapeutic benefit via topical application of an IRM for treatment of a particular condition at a particular location may be hindered due to tissue irritation, formulation wash away, poor permeation or undesired systemic delivery of the topically applied compound. Accordingly, there is a need for new methods, formulations, and systems to provide the greatest therapeutic benefit from this class of compounds.

Topical administration of a pharmacological agent to a tissue surface can provide localized therapeutic benefit without concomitant systemic effects. However, topical application is often difficult or impossible due to the anatomical location of the tissue. In some cases, application of the agent to a general anatomical region that includes or surrounds the target tissue may be an alternative to direct topical application. But, if the agent has irritating properties, this alternative disadvantageously carries with it the possibility of irritating tissues surrounding the target tissue. In addition, even if the agent is non-irritating, regional application typically requires use of a greater volume or concentration of the agent to achieve a therapeutic result equivalent to that achieved by direct application to the target tissue.

The uterine cervix is one example of a target tissue to which it is difficult to apply a topical agent. Relative to a standing position, the cervix is typically located at the uppermost portion of the vaginal cavity. However, while the cervix is located at the uppermost portion of the vaginal cavity, age, the stage of the estrous cycle, pregnancy, and other factors cause variability of the location of the cervix between different women and in the same woman at different stages of life.

Certain cervical conditions can be advantageously treated by topical administration of a pharmacological agent. Cervical dysplasia is an example of a pathological condition that can be effectively treated by direct delivery of medication to the surface of the cervix where the abnormal cells are typically found. Unfortunately, most currently available applicators for vaginal drug delivery are inadequate for applying a medication to the surface of the cervix. And, since cervical dysplasia can lead to cervical cancer, an applicator that is less than optimal is not an acceptable option.

Most presently available vaginal applicators are for application to the vaginal cavity generally and not for direct application to the cervix. In general, the length and configuration of the applicators are insufficient to ensure delivery of an agent to the uppermost portion of the vaginal cavity. Delivery to the middle or lower portion of the vagina does not ensure that an agent will reach the cervical tissue in the upper portion of the vagina. In addition, with the exception of certain body orientations, gravity tends to drain agents away from the cervix. Normal discharge and flow of fluids, both menstrual and non-menstrual, also drain away from the cervix. Thus, any applicator that is not capable of repeatedly delivering an appropriate amount of agent to the uppermost end of the vaginal cavity risks less than optimal treatment.

Overcoming the inaccuracy of present vaginal applicators, when used for cervical delivery of an agent, by delivering an excess volume or concentration of the medication may be unacceptable due to the risk of undesired effects to surrounding tissues. However, delivery of reduced volumes or concentrations to avoid irritation to surrounding tissue risks the serious consequences of ineffective treatment.

Accordingly, there is continuing need for improved delivery systems and methods for topical application of a pharmacological agent.

SUMMARY OF THE INVENTION

One aspect of the invention includes a system for treating a condition associated with a mucosal surface. The system comprises an immune response modifier (IRM) compound chosen from imidazoquinoline amines, imidazopyridine amines, 6,7-fused cycloalkylimidazopyridine amines, 1,2-bridged imidazoquinoline amines, and pharmaceutically acceptable salts thereof. The system also comprises an applicator device for applying the IRM compound to the mucosal surface.

Another aspect of the invention includes a system comprising an immune response modifier (IRM) compound chosen from imidazoquinoline amines, imidazopyridine amines, 6,7-fused cycloalkylimidazopyridine amines, imidazonaphthyridine amines, oxazoloquinoline amines, thiazoloquinoline amines, 1,2-bridged imidazoquinoline amines, and pharmaceutically acceptable salts thereof. The system also includes an applicator device for applying to the mucosal surface the IRM compound.

For example, the IRM compound may be 1-(2-methylpropyl)-1H-imidazo[4,5-c]-quinolin-4-amine, or 4-amino-α,α-dimethyl-2-ethoxymethyl-1H-imidazo[4,5-c] quinoline-1-ethanol or 2-propyl[1,3]thiazolo[4,5-c] quinolin-4-amine.

The system may be used for treating a condition associated with the mucosal surface on a cervix, optionally, the vaginal part of the cervix. Exemplary conditions associated with the mucosal surface include cervical dysphasia and cervical intraepithelial neoplasia.

In an exemplary embodiment, the applicator device may comprise a hollow tube and a piston slidably received within the tube.

Yet another aspect of the invention includes a method for treating a condition associated with a mucosal surface. The method comprises providing an immune response modifier (IRM) chosen from imidazoquinoline amines, imidazopyridine amines, 6,7-fused cycloalkylimidazopyridine amines, imidazonaphthyridine amines, oxazoloquinoline amines, thiazoloquinolines amines, 1,2-bridged imidazoquinoline amines, and pharmaceutically acceptable salts thereof. The method also includes providing an applicator device for applying to the mucosal surface the IRM compound. In addition, the method further includes applying the IRM compound to the mucosal surface with an applicator device.

The method may involve inserting the applicator device into the vagina, positioning a distal end of the applicator device adjacent to the vaginal part of the cervix, and applying the IRM compound to the vaginal part of the cervix.

At least some of the embodiments disclosed herein provide medicament application systems and methods suitable for topical administration of an agent to a target tissue. The systems and methods could be advantageous for intravaginal delivery of a pharmacological formulation. For example, some embodiments provide effective topical application of a pharmacological agent to the cervix for treatment or prevention of conditions including, for example, cervical dysplasia.

Additional aspects will be set forth in part in the description which follows, and in part will be obvious from the description, or may be learned by practice of the invention. It will be appreciated that at several locations throughout the specification, guidance is provided through lists of examples. In each instance, the recited list serves only as a representative group; it is not meant that the list is exclusive.

It is to be understood that both the foregoing general description and the following detailed description are exemplary and explanatory only and are not restrictive.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 2 is an exploded perspective view of components of a intravaginal delivery device;

FIG. 3 is a proximal end-on view of an exemplary intravaginal delivery device;

FIG. 4 is a longitudinal cross-section view of an exemplary intravaginal delivery device taken through line 4—4 with the pushing member retracted proximally;

FIG. 8 is an exploded perspective view of components of an optional alternative embodiment of an intravaginal delivery device according to the invention;

FIG. 9 is a longitudinal cross-section view of the intravaginal delivery device of FIG. 8 with the pushing member retracted proximally;

FIG. 10 is a longitudinal cross-section view of the intravaginal delivery device of FIG. 8 with the pushing member distally advanced;

FIG. 11 is a close-up view of the distal end of the intravaginal delivery device illustrated in FIG. 10;

FIG. 12 is a close-up view of the proximal end of the drug delivery device of FIG. 10;

DESCRIPTION OF THE EMBODIMENTS

Figure 1A:
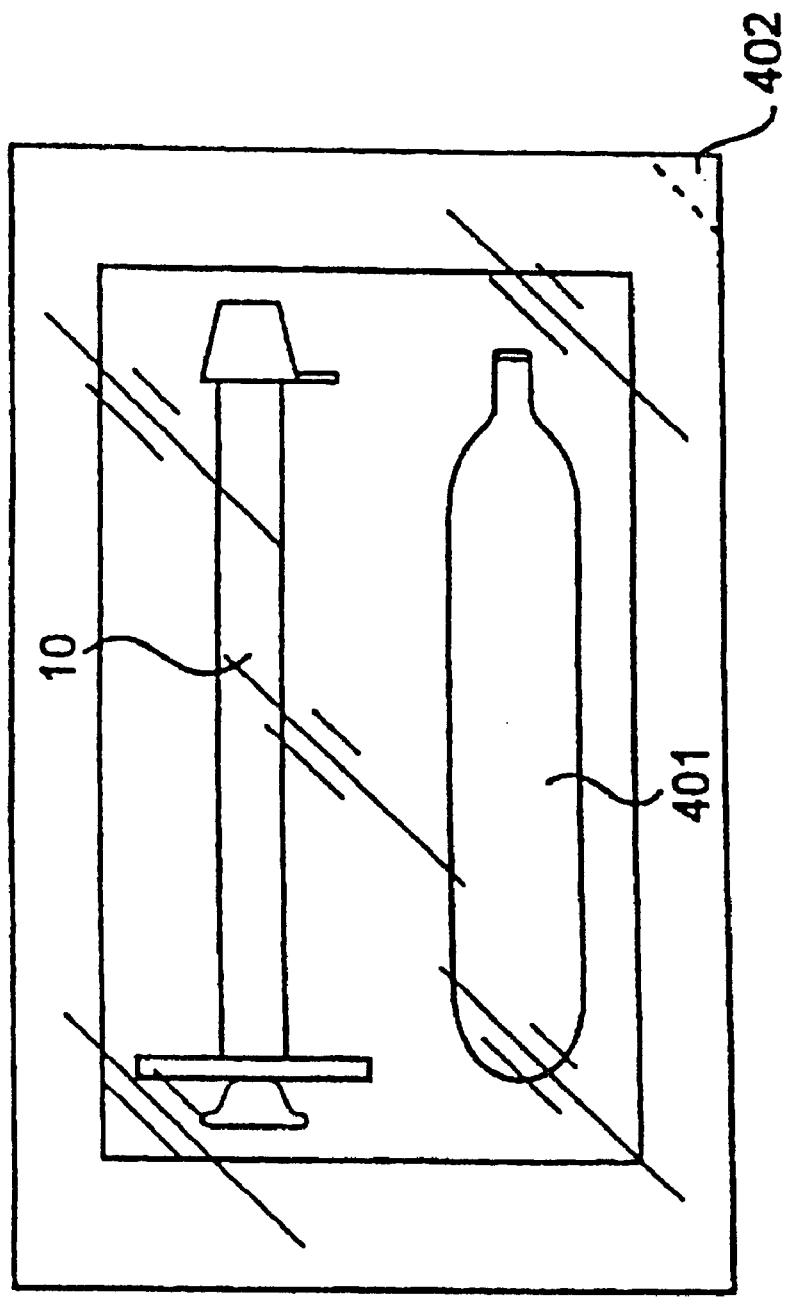
FIG. 1A is a top view of a treatment system including an applicator device and a container containing an IRM compound packaged together.

Reference will now be made in detail to some exemplary embodiments of the invention, examples of which are illustrated in the accompanying drawings. Wherever possible, the same reference numbers will be used throughout the drawings to refer to the same or like parts.

The present invention may be, in part, directed to medicament applicators and methods for delivery of a pharmacological agent to a selected location. In some optional embodiments, the dispensers may be particularly suited for intravaginal delivery of a pharmacological agent. In optional embodiments, the disclosed dispensers may provide for topical application of the pharmacological agent to an intravaginal location, such as the cervix, for treatment of conditions including, for example, cervical dysplasia. In general, the dispensers may be used to deliver a pharmacological agent in a frequency and amount necessary to obtain a desired treatment result.

Throughout the specification, guidance may be provided through lists of examples. In each instance, the recited list serves only as a representative group. It is not meant, however, that the list is exclusive.

As used herein the term "pharmacological agent" includes any agent or combination of agents that can be used to diagnose, treat, cure, ameliorate, prevent or otherwise manage a condition of a patient. The term "condition" refers to any infectious, non-infectious, pathological, physiological, biochemical or other state of a patient's body that can be treated according to the invention.

Throughout the specification, unless otherwise stated, the terms "proximal" and "distal" are relative terms. The term "proximal" refers to a location nearest the user (for example, the user's hand that is operating the dispenser) and the term "distal" refers to a location farthest from the user. Thus, in a typical embodiment, the proximal end of the delivery device will be nearest to or grasped by the hand of the user and the distal end of the instrument will be located nearest to the tissue site at which the agent will be applied.

As used herein, a "mucosal associated condition" means an inflammatory, infectious, neoplastic or other condition that involves a mucosal surface or that is in sufficient proximity to a mucosal surface to be affected by a therapeutic or prophylactic agent topically applied to the mucosal surface.

Unless stated otherwise, the term "treat", and derivatives such as "treatment", "treating", etc., are used herein generically to indicate administration of a pharmacological agent for any reason to a patient and is not intended to distinguish a preventative, therapeutic, diagnostic, palliative or other procedure. The term "therapeutically effective amount" means the amount of an agent administered to provide a desired therapeutic effect, such as cytokine induction, antiviral or antitumor activity. A "therapeutically effective amount" includes a single dose of an agent used in a course of therapy over a period of time to achieve a desired therapeutic effect.

Some optional embodiments of devices and methods of the invention may be advantageous for delivering an agent to the uterine cervix through the vagina to treat (i.e., prevent, diagnose, ameliorate, etc.) a cervical condition. In certain optional embodiments, the dispensers of the invention may be particularly advantageous for delivering an immune response modifier (IRM) to the cervix for a cervical condition. Examples of immune response modifiers suitable for the invention include those disclosed in, for example, U.S. Pat. Nos. 4,689,338; 5,389,640; 5,268,376; 4,929,624; 5,266,575; 5,352,784; 5,494,916; 5,482,936; 5,346,905; 5,395,937; 5,238,944; 5,525,612; 5,175,296; 5,693,811; 5,741,908; 5,939,090; 6,110,929; 4,988,815; 5,376,076; and PCT Publications WO 99/29693; WO 00/76505; WO 00/76518; and WO 00/76519. The entire disclosure of each of these patents and patent applications is incorporated herein by reference. Some optional IRMs suitable for the invention include 1-(2-methylpropyl)-1H-imidazo[4,5-c]quinolin-4-amine (imiquimod) and compounds and formulations such as disclosed in co-pending U.S. Ser. No. 09/479,578 and PCT Publication WO 00/06577. The entire disclosure of each of these patents and applications are incorporated herein by reference.

In general, the "user" of the disclosed dispensers (also referred to herein as applicators) include health care providers who apply the agent to a patient or the patient themselves for self-administration of the agent.

In some optional embodiments, the dispensers can provide for accurate delivery of a predetermined amount of the pharmacological agent to a selected location with reduced likelihood of inadvertent delivery to surrounding tissues. Typically, a predetermined amount is a therapeutically effective amount for a single dose. Accurate application of the agent to a selected location can advantageously reduce the amount of the agent necessary to achieve a therapeutic result while minimizing the possibility of irritation to tissues adjacent to the selected site of application.

In the case of intravaginal applications, the dispenser may reduce undesired side effects caused by an agent. For example, when delivery of an agent is desired only to the cervix, such as for a cervical condition, delivery of the agent to locations other than the upper portion of the vaginal cavity can unnecessarily expose the lower vaginal cavity and other surrounding tissues to the agent. This not only exposes non-targeted tissues to the agent, but also to potential tissue irritation that can be caused by the agent or other components in a pharmacological formulation.

The intravaginal dispensers may optionally provide for accurate delivery of a volume of an agent (or formulation thereof) that is smaller than volumes typically used for administering other intravaginal medications. In some optional embodiments, the intravaginal dispensers may provide for delivery of about 0.01–10 ml, in other optional embodiments about 0.5 to 4 ml and typically about 1.0 ml.

The dispensers can be pre-filled with a therapeutically effective amount of a particular agent or filled by the user at the time of administration. In the latter situation, the dispensers can be configured to receive the agent from a source of the agent (e.g., aluminum tube, plastic tube, etc.) that can mount to the dispenser for filling. Some optional dispensers may typically provide for a fixed maximum volume of the agent. Alternatively, or additionally, the dispensers can have incremental markings for filling with amounts less than the maximum volume of the dispenser.

In an optional embodiment, a pre-filled dispenser may be provided to eliminate the possibility of filling the delivery device with an incorrect amount of the agent. In one optional embodiment, the dispensers may be pre-filled with a formulation including an amount of immune response modifier (IRM) compound for a single treatment. The dispenser, whether pre-filled or not, may be packaged in an outer wrap, such as a foil wrap, which maintains sterility and can act as a moisture barrier.

The dispenser may be formed through known methods including injection molding processes that form a plastic applicator from polymer materials such as high density polyethylene, low density polyethylene, linear low density polyethylene, or polypropylene.

FIG. 1A shows a treatment system 400 including an applicator device 10 and a container 401 of a formulation packaged together in packaging 402. The device 10 could be configured to be filled with formulation contained in the container 401 by placing them in flow communication with one another.

Figure 1B:
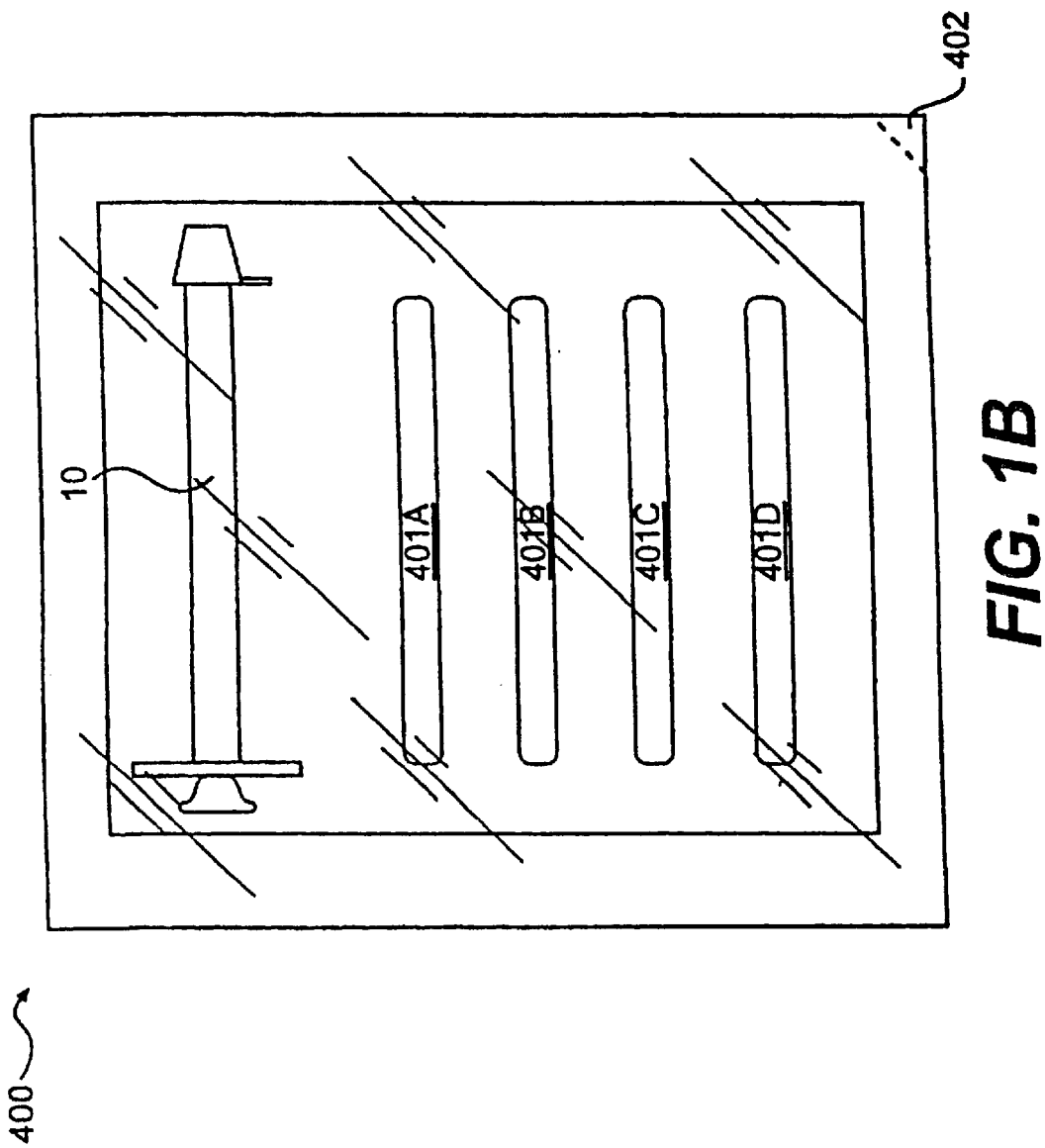
FIG. 1B is a top view of a treatment system with several pre-filled cartridges of the IRM compound.

FIG. 1B shows a treatment system 400 where the formulation is a contained in pre-filled cartridges 401a–401d capable of being loaded in the dispensing device 10 one at a time.

FIGS. 2 and 4 show an optional embodiment of an intravaginal delivery device 10 according to the invention. As illustrated, device 10 may include a distal end 1, a proximal end 2 and a longitudinal axis X—X passing therethrough. FIG. 2 is an exploded perspective view of components of device 10 including elongate tube 3 having a delivery end 4, an operating end 5 and a lumen 6 passing therethrough. Operating end 5 can include handle arrangement 7 such as opposing flanges 8a and 8b for holding device 10 during use. In some embodiments, elongate tube 3 may have a length dimension of about 6 cm to about 24 cm, typically, about 10 cm to about 18 cm.

Pushing member 11 may be slidably received within lumen 6 of elongate tube 3 and may include a pushing end 12 and a driving end 13. Pushing end 12 may include a platform 14 for placement of a user's thumb or finger to distally advance pushing member 11 within lumen 6. Piston 15 may be mountable to driving end 13 of pushing member 11 and may have a distal tip 16 opposite end 17. A cap 18 may be removably mounted to the distal end 4 of device 10 using known arrangements such as threads or friction fit, for example.

FIG. 3 is a distal end view of device 10 and FIG. 4 is a longitudinal cross-section of device 10 taken through line 4—4 of FIG. 3. In FIG. 4, piston 15 is shown mounted to the driving end 13 of pushing member 11 and located at a first position that provides a chamber 20 for containing or receiving a predetermined amount of a pharmacological agent.

In some optional embodiments, chamber 20 will provide for a volume of a pharmacological agent of about 5 ml to 0.1 ml, typically about 2 ml to 0.5 ml and optionally about 1.0 ml. In an optional embodiment, the driving end 13 of pushing member 11 may be removably nested into bore 19 of piston 15. Thus, in this optional embodiment, if pushing member 11 is retracted proximally the driving end 13 of pushing member 11 may pull free from bore 19 and piston 15 will not be retracted proximally with pushing member 11. This optional aspect may prevent aspiration of an agent after expulsion of the agent from chamber 20 and may also prevent aspiration of tissue into the delivery end 4 of tube 3 if pushing member 11 is retracted proximally.

In addition, in some optional embodiments, lumen 6 may include a stop 40, such as protuberance 41 which may protrude into lumen 6 to prevent proximal retraction of piston 15. Whether device 10 is pre-filled with an agent or filled by the user at the time of use, the position of stop 40 may provide a fixed maximum volume of chamber 20 to contain a predetermined amount of an agent. This stop can advantageously prevent a user from exceeding a particular dose of an agent if the device 10 is filled with the agent by the user prior to use.

Cap 18 is shown mounted at delivery end 4. Cap 18 can be friction fit to the external surface 35 of delivery end 4. Alternatively, or in addition, cap 18 can include a stem 18a which is friction fit into the distal end 1 of lumen 6. Distal end 1 of lumen 6 could alternatively have female threads (not shown) which can threadedly receive male threads (not shown) which can be present on the exterior surface of stem 18a. Cap 18 can also include a tab 18b which provides for easier gripping of cap 18 when removing from tube 3.

Cap 18, could optionally include texturing, such as knurls, ridges, etc., to facilitate removal. Markings, such as a raised arrow, can optionally be added to the cap 18 to indicate the direction to unscrew for removal to contribute to the ease of use of the device.

Figure 5:
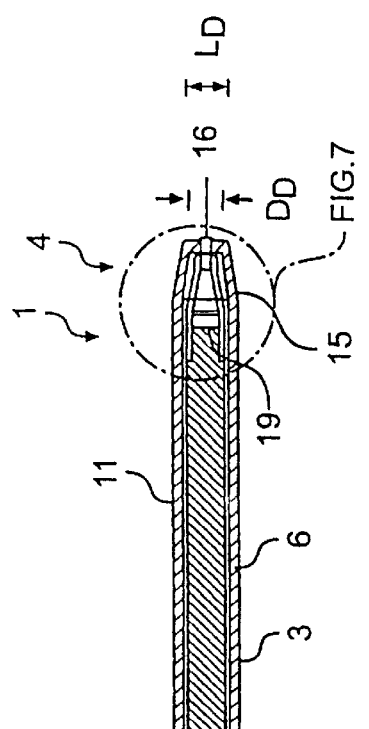
FIG. 5 is a longitudinal cross-section of an exemplary intravaginal delivery device with the pushing member advanced distally.

In FIG. 5, pushing member 11 has been distally advanced to a position that would cause expulsion of a pharmacological agent from chamber 20. In the optional illustrated embodiment, when pushing member 11 is distally advanced, the distal tip 16 of piston 15 protrudes beyond the distal end 4 of elongate tube 3. In addition, distal tip 16 can be convex shaped or domed outwardly to further ensure complete expulsion of an agent from chamber 20.

Figure 6:
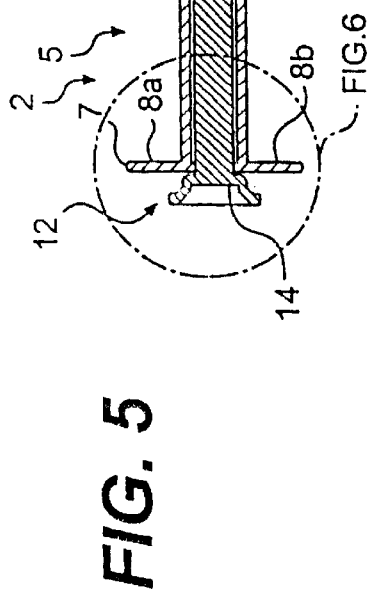
FIG. 6 is a close-up view of the proximal end of the intravaginal delivery device illustrated in FIG. 5.

FIG. 6 is a close-up view of an optional embodiment of a proximal end 2 of delivery device 10. In the illustrated embodiment, platform 14 of pushing member 11 forms a shoulder 25 at the junction with the pushing end 12 of pushing member 11. When pushing member 11 is distally advanced within lumen 6, shoulder 25 may affirmatively stop by abutting against the operating end 5 of elongate tube 3 which may indicate complete delivery of a pharmacological agent from chamber 20 of device 10.

Figure 7:
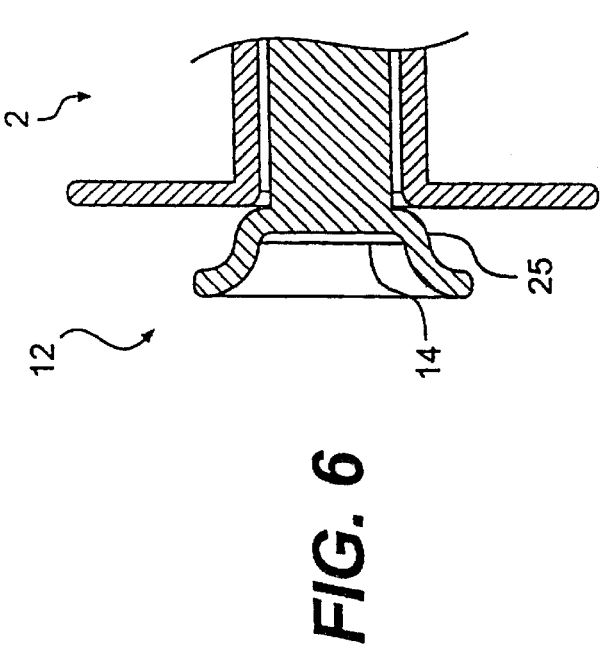
FIG. 7 is a close-up view of the distal end of the intravaginal delivery device illustrated in FIG. 5.

FIG. 7 is a close-up of an optional embodiment of a distal end 1 of delivery device 10. As illustrated, the distal end of chamber 20 of lumen 6 may include a converging taper 30. The external surface 31 of piston 15 may also have a converging taper 32 that may extend to distal tip 16. The corresponding converging tapers 30 and 32 may facilitate complete delivery of a pharmacological agent contained within chamber 20 when pushing member 11 is advanced distally. Piston 15 also may include a sealing ring 33 such as circumferential flange 34 which may fit snugly against lumen 6 to assure that a significant portion, preferably all, of the pharmacological agent is removed from lumen 6 as piston 15 is advanced distally. Thus, lumen 6 may have at least two different diameters, a lumen diameter $L_D$ and a delivery diameter $D_D$. A typical lumen diameter $L_D$ may be about 5 to about 15 mm and a typical delivery diameter may be about 2 to about 10 mm. In an example of a delivery device 10 with a maximum chamber volume of about 1 ml, the length of elongate tube 3 can be about 12–20 cm, $L_D$ can be about 10 mm and $D_D$ can be about 6 mm.

The external surface 35 of distal end 1 of elongate tube 3 may also have a converging taper 36 to facilitate insertion of the distal end 1 of device 10 into the vagina. After expulsion of an agent from chamber 20, converging taper 36 may also ensure that all of the dispensed agent remains at the site of delivery. For example, when delivering an agent to the cervix, the vaginal wall surrounding the distal end 1 can drape closely around the distal tip 1 to wipe off any of the agent remaining on the tip as compared to applicators having a square-ended (i.e., right cylinder) tip or square-ended tip with rounded corners.

In use, the user can place the thumb and middle finger proximal to flanges 8a and 8b of handle arrangement 7 to hold device 10 at a selected location while the user's index finger is placed on platform 14 to distally advance pushing member 11 such that distal tip 16 of piston 15 expels the pharmacological agent from chamber 20 to deliver the agent to an intravaginal location, such as the mucosal surface of the cervix.

FIG. 8 is an exploded perspective view of the components of an optional alternative embodiment of an intravaginal delivery device 100. As illustrated, delivery device 100 may include a proximal end 101, a distal end 102 and a longitudinal axis X—X passing therethrough. Elongate tube 103 may have a delivery end 104, an operating end 105 and a lumen 106 passing therethrough. A cap 108 can be slidably or threadedly mounted to distal end 102 of device 100 as described above for cap 18 of device 10.

The operating end 105 of elongate tube 103 may include a handle arrangement 107 including tip 118 to facilitate handling of device 100 during use. In the optional illustrated embodiment, lip 118 may extend continuously around the circumference of the operating end 105. However, it will be appreciated that lip 118 need not be continuous and, in other embodiments, lip 118 can be omitted.

Pushing member 111 can be slidably received into lumen 106 and may include a pushing end 113, driving end 114 and a shaft 115 extending therebetween. The pushing end 113 can include a platform 116 for placement of a user's thumb or finger to distally advance pushing member 111 during use. Platform 116 can have a concave surface 117 to better conform to the tip of a user's finger or thumb. Piston 120 can be fixedly mounted to driving end 114 of pushing member 111 or driving end 114 can be removably nested into bore 122a at end 122. Piston 120 may include a distal tip 121. In some embodiments, distal tip 121 can be convexed distally or domed outwardly to further ensure complete expulsion of the agent.

FIG. 9 is a longitudinal cross-section view of device 100 showing chamber 130 for containing or receiving a predetermined amount of a pharmacological agent when pushing member 111 is proximally retracted within lumen 106 of elongate tube 103. FIG. 10 illustrates that when pushing member 111 is distally advanced, the distal tip 121 of piston 120 may extend beyond the distal end 102 of elongate tube 103.

FIG. 11 is a close-up view of the distal end 102 of the view of device 100 illustrating that chamber 130 may include a converging taper 131 at the distal end 102 of lumen 106. The optional converging taper 131 of chamber 130 may be configured to match with a corresponding converging taper 132 in a distal portion of piston 120. The converging surfaces 131 and 132 may facilitate complete expulsion of a pharmacological agent contained within chamber 130.

Piston 120 also can include a sealing ring 133 such as circumferential flange 134 which may fit snugly against lumen 106 to ensure complete expulsion of the agent as piston 120 is advanced distally. The external surface 135 of the distal end 102 of elongate tube 103 may be tapered 136 for reasons discussed above.

As with device 10, in some optional embodiments, lumen 106 can include a stop 140 such as protuberance 141 which may protrude into lumen 106 to prevent proximal retraction of piston 120. Whether device 100 is pre-filled with an agent or filled by the user at the time of use, the position of stop 140 may provide a fixed maximum volume of chamber 130 to contain a predetermined amount of an agent.

FIG. 12 is a close-up view of an optional embodiment of a proximal end 101 of device 100 of FIG. 10 illustrating that when pushing member 111 is fully advanced distally, platform 116 of pushing end 113 may be recessed within the operating end 105 of elongate tube 103. This feature reduces the likelihood that some or all of the pharmacological agent dispensed from chamber 130 will be aspirated back into the chamber 130 after delivery by inadvertent proximal retraction of pushing member 111 after the pharmacological agent has been expelled.

Also, in some optional embodiments, the operating end 105 of elongate tube 103 and the pushing end 113 of pushing member 111 can be constructed to provide audible and/or tactile feedback to the user when expulsion of the agent is complete. According to this optional embodiment, the operating end 105 of lumen 106 can include a projecting surface 145 such as ridge 146 at a location proximal to platform 116 when pushing member 111 is fully advanced distally. Platform 116 may be sized such that as platform 116 is pushed distally past ridge 146 a click can be heard and the movement past ridge 146 creates a tactile click to inform the user of complete expulsion of the agent. Ridge 146 may also act to "lock" pushing member 111 in the distally advanced portion and may prevent proximal retraction of pushing member 111.

It will be appreciated that in addition to lumen diameter $L_D$ and delivery diameter $D_D$, lumen 106 also has a diameter $P_O$ at operating end 105. Lumen 106 thus may have a taper 150 extending between diameter $P_O$ and $L_D$. In an example of a delivery device 100 having a maximum chamber volume of about 1 ml, the length of elongate tube 103 is about 15 to about 17 cm, $L_D$ is about 11–15 mm and $D_D$ is about 7–12 mm.

In an optional alternative embodiment, the region of elongate tube 103, shown as having parallel sides (see e.g., FIG. 9) extending from the proximal end to the distal end, can alternatively have a converging taper from the proximal end to distal end. This may advantageously provide for filling the delivery device with a pharmacological agent from the proximal end of elongate tube rather than the distal end. That is, without a taper as just described, attempting to push the piston into place distally along a non-tapered tube, after loading the formulation could be hindered by air that can be trapped between the piston seal and wall of the lumen. By tapering the elongate lumen as described, a gap may be maintained between the piston and the wall that may allow for air to escape as the piston is advanced distally. Such a taper could occur gradually over the length of the elongate tube, or there can be an abrupt taper near where the piston is to be placed for setting a predetermined volume at the distal end of the elongate tube.

Figure 13:
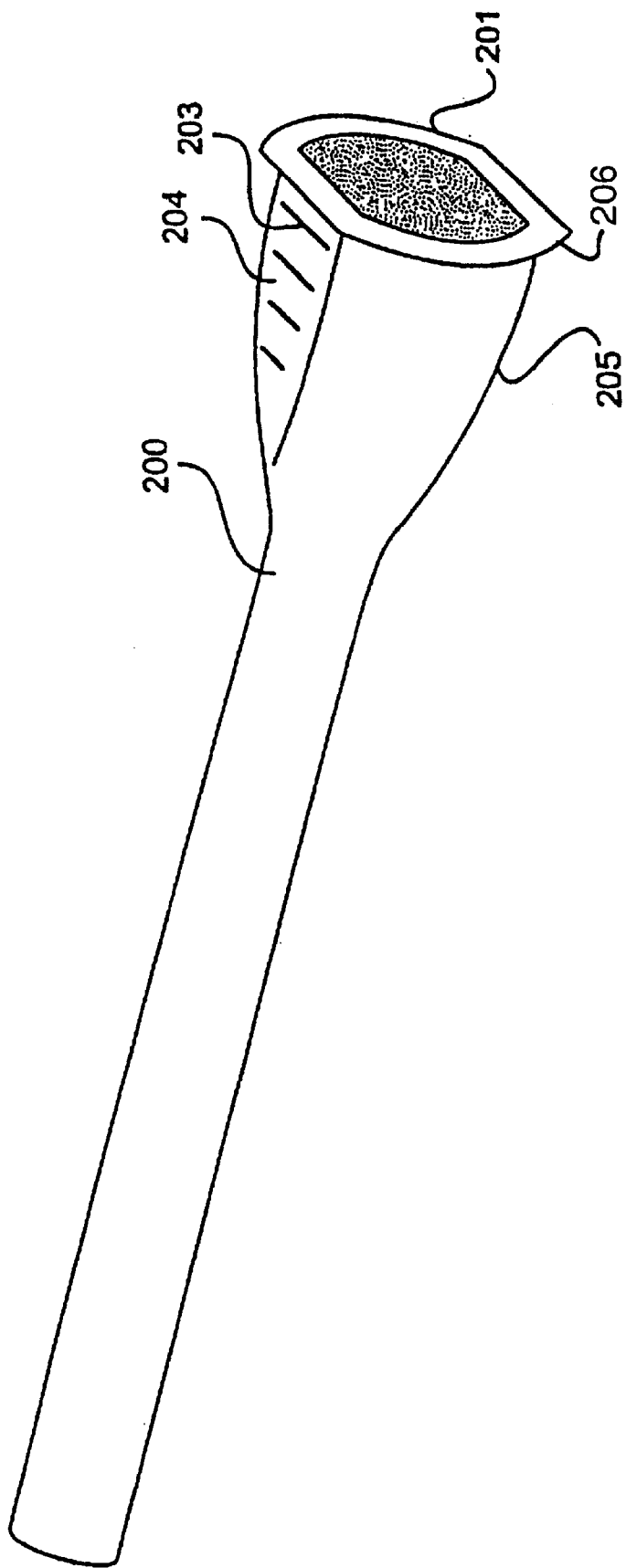
FIG. 13 is a perspective view of an alternative proximal end for an intravaginal delivery device.

FIG. 13 illustrates another optional embodiment of the operating end of an elongate tube suitable for an intravaginal delivery device 10, 100 according to the invention. According to this embodiment, the operating end 201 of elongate tube 200 may include a configuration which provides an indicator 203 of the orientation of device 200 around longitudinal axis X—X. Thus, in the embodiment of FIG. 13, some opposing sides 204 and 205 are linear giving the operating end an oval cross-sectional configuration. In this embodiment, lip 206 may extend around the perimeter of the operating end 201. It will be appreciated, however, that the lip may be completely absent or discontinuous around the perimeter.

Figure 14:
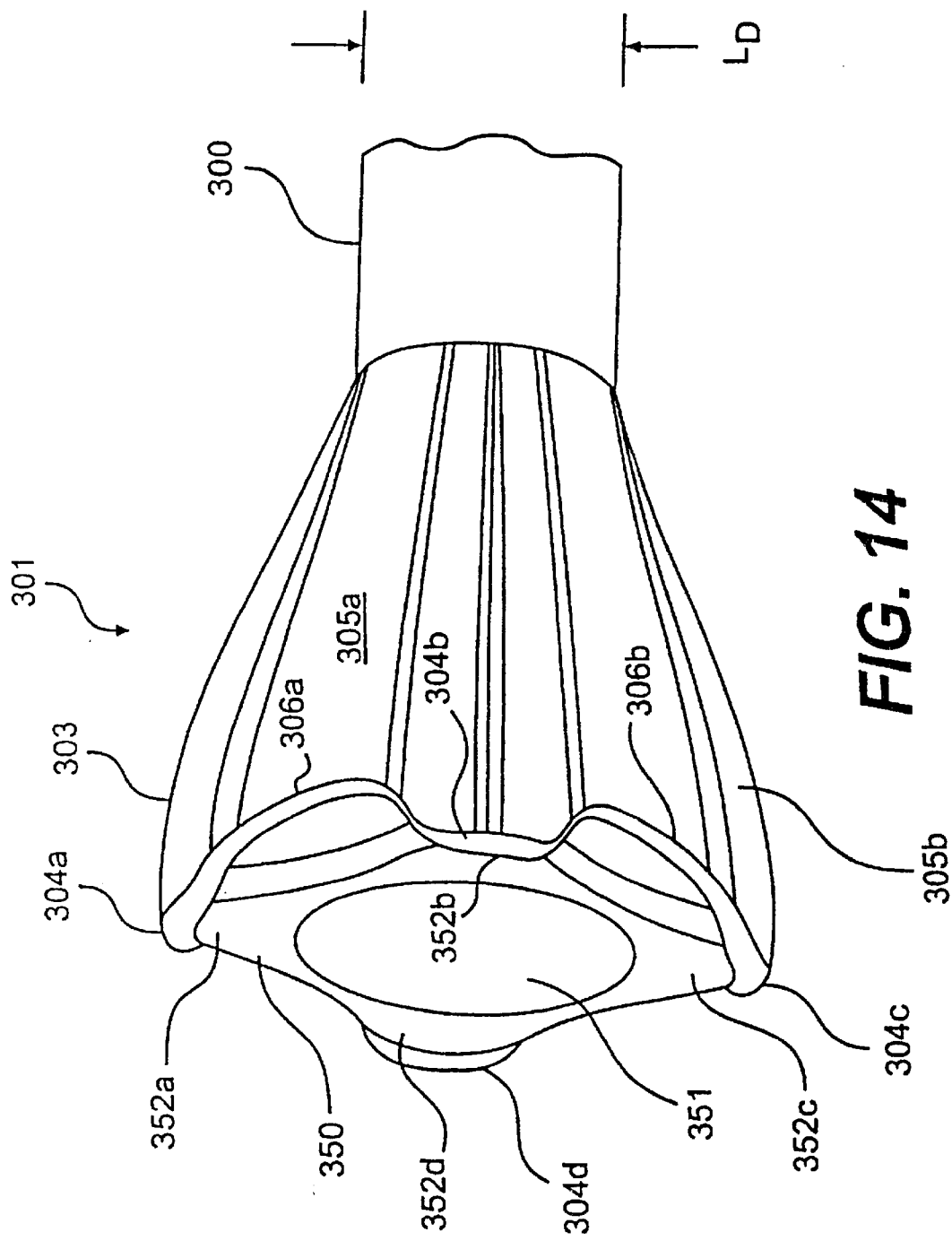
FIG. 14 is a perspective view of another alternative proximal end for an intravaginal delivery device.

FIG. 14 illustrates another optional embodiment of the operating end of an elongate tube 300 suitable for an intravaginal delivery device according to the invention. In this embodiment, the operating end 301 of elongate tube 300 may include a configuration which also provides an indicator 303 for the orientation of device 300 around longitudinal axis X—X. Operating end 301 may include corners 304a–304d. The walls 305a–305d of operating end 301 between corners 304a–304d form a converging taper moving from operating end diameter $P_O$ to lumen diameter $L_D$. In the illustrated embodiment, the proximal aspect of each of walls 305a–305d may include a concave void 306a–306d extending distally into the surface of the walls 305a–305d, respectively. In addition, the platform 350 of the pushing member (not visible) may have a distally concave surface 351 and four corners 352a–352d configured to mate with the corners 304a–304d of walls 305a–305d. A lip or flanges (not shown in this embodiment) may or may not be present around the proximal edge of the operating end 301 as described for device 10 and 110.

The intravaginal delivery device may provide for accurate delivery of a volume of an agent that is less than the volumes typically used for other vaginal medications. Many vaginal applicators are designed to deliver about 5 ml of an agent and the application is not localized but rather it is delivered to the vaginal cavity in general.

Figure 15:
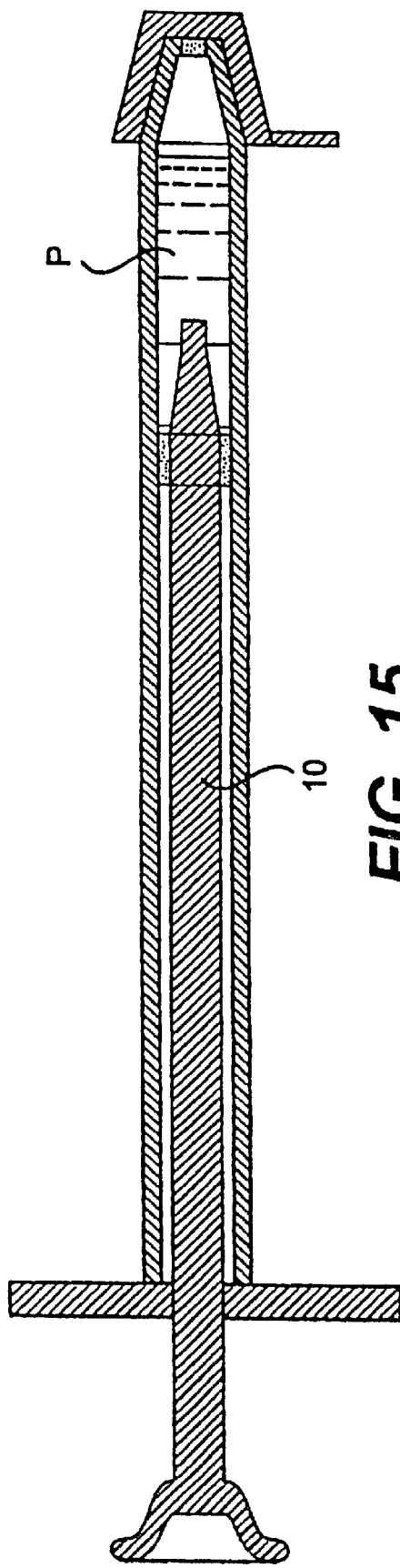
FIG. 15 is a longitudinal cross section view of an exemplary intravaginal delivery device pre-filled with a formulation.

In optional embodiments, such as that shown in FIG. 15, the applicator 10 may be pre-filled with a product P to eliminate the possibility of incorrect filling of the applicator. However, if the device is to be filled at the time of use, structure such as stops in the device, may set a maximum volume that can help to eliminate the chance of exceeding a predetermined dosage.

Any of the above-mentioned applicators may have a length sufficient to allow the distal end of the applicator to be located at, or very close to, the cervix while a portion of the applicator passes through the vagina and proximal end is positioned outside the vagina. The length of the applicator may be configured to assure delivery of an IRM compound to the uppermost end of the vaginal cavity while the proximal end is outside the vagina. For example, the length of the applicator may be sufficient to accommodate anatomical variability among women, so that treatment of women with longer vaginal cavities will not be compromised.

In use, the intravaginal delivery device could be held at the proximal end between the thumb and middle finger and the platform of the pushing member depressed (i.e., advanced distally) with the index finger to deliver the agent.

In optional embodiments, the pushing member may be pre-positioned within the lumen of the elongate tube, ready for use. If the delivery device is to be filled prior to use, the distal end of the elongate tube can include female threads to fit with male threads of a medicament source, such as an aluminum tube, to provide a threaded seal while transferring the medicament from the source to the chamber of the delivery device.

The dispensers can be packaged in an overwrap pouch that provides for asepsis as well as a moisture barrier. The overwrap pouch can be made from any material suitable for protecting the pharmacological agent such as foils or foil laminates (e.g., a metal and plastic layer). In some embodiments, the overwrap can protect against moisture loss from the formulation or oxidation of the formulation.

The applicator device could be part of a system or component used in a method involving additional parts or components. In one optional embodiment, the systems and methods include an immune response modifier (IRM) compound to treat or prevent conditions associated with a mucosal surface. For example, the IRM compound could be in a formulation which can be applied to the mucosal surface of the cervix to treat cervical conditions including cervical dysplasias such as cervical intraepithelial neoplasia.

In some optional embodiments, the certain formulations may be used for application of an IRM compound to a mucosal surface. In some optional embodiments, the formulations can enhance therapeutic efficiency of the IRM by facilitating mucosal permeation or increasing the duration of contact of the IRM with the mucosal surface. The pharmaceutical formulation may contain a preservative system that renders the formulations suitable for packaging in multiple-use containers.

IRM Compounds

As noted above, many of the imidazoquinoline amine, imidazopyridine amine, 6,7-fused cycloalkylimidazopyridine amine, 1,2-bridged imidazoquinoline amine, thiazolo- and oxazolo-quinolinamines and pyridinamines, imidazonaphthyridine and tetrahydroimidazonaphthyridine amine IRM compounds of the present invention have demonstrated significant immunomodulating activity. Some optional immune response modifier compounds of the invention include 1H-imidazo[4,5-c]quinolin-4-amines defined by one of Formulas I–V below:

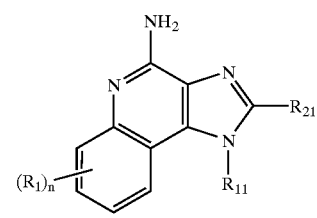

I wherein
$R_{11}$ is selected from the group consisting of alkyl of one to ten carbon atoms, hydroxyalkyl of one to six carbon atoms, acyloxyalkyl wherein the acyloxy moiety is alkanoyloxy of two to four carbon atoms or benzoyloxy, and the alkyl moiety contains one to six carbon atoms, benzyl, (phenyl)ethyl and phenyl, said benzyl, (phenyl)ethyl or phenyl substituent being optionally substituted on the benzene ring by one or two moieties independently selected from the group consisting of alkyl of one to four carbon atoms, alkoxy of one to four carbon atoms and halogen, with the proviso that if said benzene ring is substituted by two of said moieties, then said moieties together contain no more than six carbon atoms;

$R_{21}$ is selected from the group consisting of hydrogen, alkyl of one to eight carbon atoms, benzyl, (phenyl)ethyl and phenyl, the benzyl, (phenyl)ethyl or phenyl substituent being optionally substituted on the benzene ring by one or two moieties independently selected from the group consisting of alkyl of one to four carbon atoms, alkoxy of one to four carbon atoms and halogen, with the proviso that when the benzene ring is substituted by two of said moieties, then the moieties together contain no more than six carbon atoms; and each $R_1$ is independently selected from the group consisting of alkoxy of one to four carbon atoms, halogen, and alkyl of one to four carbon atoms, and n is an integer from 0 to 2, with the proviso that if n is 2, then said $R_1$ groups together contain no more than six carbon atoms;

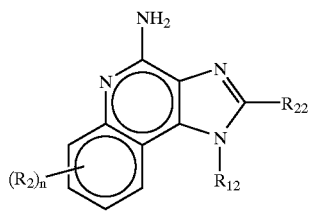

II wherein $R_{12}$ is selected from the group consisting of straight chain or branched chain alkenyl containing two to ten carbon atoms and substituted straight chain or branched chain alkenyl containing two to ten carbon atoms, wherein the substituent is selected from the group consisting of straight chain or branched chain alkyl containing one to four carbon atoms and cycloalkyl containing three to six carbon atoms; and cycloalkyl containing three to six carbon atoms substituted by straight chain or branched chain alkyl containing one to four carbon atoms; and $R_{22}$ is selected from the group consisting of hydrogen, straight chain or branched alkyl containing one to eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to four carbon atoms, straight chain or branched chain alkoxy containing one to four carbon atoms, and halogen, with the proviso that when the benzene ring is substituted by two such moieties, then the moieties together contain no more than six carbon atoms; and each $R_2$ is independently selected from the group consisting of straight chain or branched chain alkoxy containing one to four carbon atoms, halogen, and straight chain or branched chain alkyl containing one to four carbon atoms, and n is an integer from zero to 2, with the proviso that if n is 2, then said $R_2$ groups together contain no more than six carbon atoms;

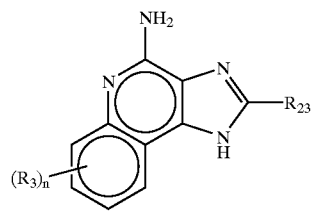

III wherein $R_{23}$ is selected from the group consisting of hydrogen, straight chain or branched chain alkyl of one to eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl of one to four carbon atoms, straight chain or branched chain alkoxy of one to four carbon atoms, and halogen, with the proviso that when the benzene ring is substituted by two such moieties, then the moieties together contain no more than six carbon atoms; and each $R_3$ is independently selected from the group consisting of straight chain or branched chain alkoxy of one to four carbon atoms, halogen, and straight chain or branched chain alkyl of one to four carbon atoms, and n is an integer from zero to 2, with the proviso that if n is 2, then said $R_3$ groups together contain no more than six carbon atoms;

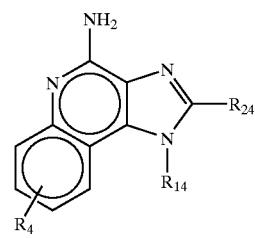

IV wherein $R_{14}$ is —$CHR_xR_y$ wherein $R_y$ is hydrogen or a carbon-carbon bond, with the proviso that when $R_y$ is hydrogen $R_x$ is alkoxy of one to four carbon atoms, hydroxyalkoxy of one to four carbon atoms, 1-alkynyl of two to ten carbon atoms, tetrahydropyranyl, alkoxyalkyl wherein the alkoxy moiety contains one to four carbon atoms and the alkyl moiety contains one to four carbon atoms, 2-, 3-, or 4-pyridyl, and with the further proviso that when $R_y$ is a carbon-carbon bond $R_y$ and $R_x$ together form a tetrahydrofuranyl group optionally substituted with one or more substituents independently selected from the group consisting of hydroxy and hydroxyalkyl of one to four carbon atoms;

$R_{24}$ is selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen; and $R_4$ is selected from the group consisting of hydrogen, straight chain or branched chain alkoxy containing one to four carbon atoms, halogen, and straight chain or branched chain alkyl containing one to four carbon atoms;

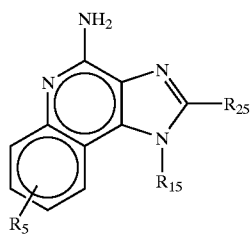

wherein
  $R_{15}$ is selected from the group consisting of: hydrogen; straight chain or branched chain alkyl containing one to ten carbon atoms and substituted straight chain or branched chain alkyl containing one to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; straight chain or branched chain alkenyl containing two to ten carbon atoms and substituted straight chain or branched chain alkenyl containing two to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to four carbon atoms, alkoxy of one to four carbon atoms, and halogen, with the proviso that when said benzene ring is substituted by two of said moieties, then the moieties together contain no more than six carbon atoms;
  $R_{25}$ is

wherein
  $R_S$ and $R_T$ are independently selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen;
  X is selected from the group consisting of alkoxy containing one to four carbon atoms, alkoxyalkyl wherein the alkoxy moiety contains one to four carbon atoms and the alkyl moiety contains one to four carbon atoms, hydroxyalkyl of one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, chloro, hydroxy, 1-morpholino, 1-pyrrolidino, alkylthio of one to four carbon atoms; and
  $R_5$ is selected from the group consisting of hydrogen, straight chain or branched chain alkoxy containing one to four carbon atoms, halogen, and straight chain or branched chain alkyl containing one to four carbon atoms;
or a pharmaceutically acceptable salt of any of the foregoing.

Preferred 6,7 fused cycloalkylimidazopyridine amine IRM compounds are defined by Formula VI below:

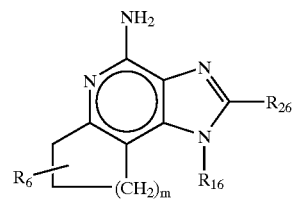

wherein m is 1, 2, or 3;
  $R_{16}$ is selected from the group consisting of hydrogen; cyclic alkyl of three, four, or five carbon atoms; straight chain or branched chain alkyl containing one to ten carbon atoms and substituted straight chain or branched chain alkyl containing one to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; fluoro- or chloroalkyl containing from one to ten carbon atoms and one or more fluorine or chlorine atoms; straight chain or branched chain alkenyl containing two to ten carbon atoms and substituted straight chain or branched chain alkenyl containing two to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms, with the proviso that any such alkyl, substituted alkyl, alkenyl, substituted alkenyl, hydroxyalkyl, alkoxyalkyl, or acyloxyalkyl group does not have a fully carbon substituted carbon atom bonded directly to the nitrogen atom; benzyl; (phenyl)ethyl; and phenyl; said benzyl, (phenyl)ethyl or phenyl substituent being optionally substituted on the benzene ring by one or two moieties independently selected from the group consisting of alkyl of one to four carbon atoms, alkoxy of one to four carbon atoms, and halogen, with the proviso that when said benzene ring is substituted by two of said moieties, then the moieties together contain no more than six carbon atoms;

and —$CHR_xR_y$ wherein
- $R_y$ is hydrogen or a carbon-carbon bond, with the proviso that when $R_y$ is hydrogen $R_x$ is alkoxy of one to four carbon atoms, hydroxyalkoxy of one to four carbon atoms, 1-alkynyl of two to ten carbon atoms, tetrahydropyranyl, alkoxyalkyl wherein the alkoxy moiety contains one to four carbon atoms and the alkyl moiety contains one to four carbon atoms, 2-, 3-, or 4-pyridyl, and with the further proviso that when $R_y$ is a carbon-carbon bond $R_y$ and $R_x$ together form a tetrahydrofuranyl group optionally substituted with one or more substituents independently selected from the group consisting of hydroxy and hydroxyalkyl of one to four carbon atoms,
- $R_{26}$ is selected from the group consisting of hydrogen, straight chain or branched chain alkyl containing one to eight carbon atoms, straight chain or branched chain hydroxyalkyl containing one to six carbon atoms, morpholinoalkyl, benzyl, (phenyl)ethyl and phenyl, the benzyl, (phenyl)ethyl or phenyl substituent being optionally substituted on the benzene ring by a moiety selected from the group consisting of methyl, methoxy, and halogen; and
- —$C(R_S)(R_T)(X)$ wherein $R_S$ and $R_T$ are independently selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen;
- X is selected from the group consisting of alkoxy containing one to four carbon atoms, alkoxyalkyl wherein the alkoxy moiety contains one to four carbon atoms and the alkyl moiety contains one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, alkylthio of one to four carbon atoms, and morpholinoalkyl wherein the alkyl moiety contains one to four carbon atoms, and
- $R_6$ is selected from the group consisting of hydrogen, fluoro, chloro, straight chain or branched chain alkyl containing one to four carbon atoms, and straight chain or branched chain fluoro- or chloroalkyl containing one to four carbon atoms and at least one fluorine or chlorine atom;

and pharmaceutically acceptable salts thereof.

Preferred imidazopyridine amine IRM compounds are defined by Formula VII below:

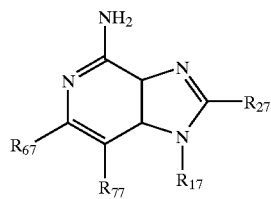

VII wherein
- $R_{17}$ is selected from the group consisting of hydrogen; —$CH_2R_W$ wherein $R_W$ is selected from the group consisting of straight chain, branched chain, or cyclic alkyl containing one to ten carbon atoms, straight chain or branched chain alkenyl containing two to ten carbon atoms, straight chain or branched chain hydroxyalkyl containing one to six carbon atoms, alkoxyalkyl wherein the alkoxy moiety contains one to four carbon atoms and the alkyl moiety contains one to six carbon atoms, and phenylethyl; and —$CH=CR_ZR_Z$ wherein each $R_Z$ is independently straight chain, branched chain, or cyclic alkyl of one to six carbon atoms;
- $R_{27}$ is selected from the group consisting of hydrogen, straight chain or branched chain alkyl containing one to eight carbon atoms, straight chain or branched chain hydroxyalkyl containing one to six carbon atoms, alkoxyalkyl wherein the alkoxy moiety contains one to four carbon atoms and the alkyl moiety contains one to six carbon atoms, benzyl, (phenyl)ethyl and phenyl, the benzyl, (phenyl)ethyl or phenyl substituent being optionally substituted on the benzene ring by a moiety selected from the group consisting of methyl, methoxy, and halogen; and morpholinoalkyl wherein the alkyl moiety contains one to four carbon atoms;
- $R_{67}$ and $R_{77}$ are independently selected from the group consisting of hydrogen and alkyl of one to five carbon atoms, with the proviso that $R_{67}$ and $R_{77}$ taken together contain no more than six carbon atoms, and with the further proviso that when $R_{77}$ is hydrogen then $R_{67}$ is other than hydrogen and $R_{27}$ is other than hydrogen or morpholinoalkyl, and with the further proviso that when $R_{67}$ is hydrogen then $R_{77}$ and $R_{27}$ are other than hydrogen;

and pharmaceutically acceptable salts thereof.

Preferred 1,2-bridged imidazoquinoline amine IRM compounds are defined by Formula VIII below:

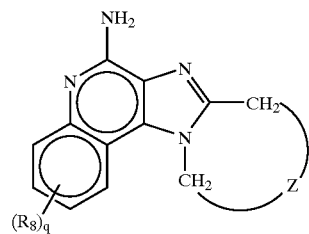

VIII wherein
Z is selected from the group consisting of:
- —$(CH_2)_p$— wherein p is 1 to 4;
- —$(CH_2)_a$—$C(R_DR_E)(CH_2)_b$—, wherein a and b are integers and a+b is 0 to 3, $R_D$ is hydrogen or alkyl of one to four carbon atoms, and $R_E$ is selected from the group consisting of alkyl of one to four carbon atoms, hydroxy, —$OR_F$ wherein $R_F$ is alkyl of one to four carbon atoms, and —$NR_GR'_G$ wherein $R_G$ and $R'_G$ are independently hydrogen or alkyl of one to four carbon atoms; and
- —$(CH_2)_a$—$(Y)$—$(CH_2)_b$— wherein a and b are integers and a+b is 0 to 3, and Y is O, S, or —$NR_J$— wherein $R_J$ is hydrogen or alkyl of one to four carbon atoms;

and wherein q is 0 or 1 and $R_8$ is selected from the group consisting of alkyl of one to four carbon atoms, alkoxy of one to four carbon atoms, and halogen, and pharmaceutically acceptable salts thereof.

Suitable thiazolo- and oxazolo-quinolinamine and pyridinamine compounds include compounds of Formula IX:

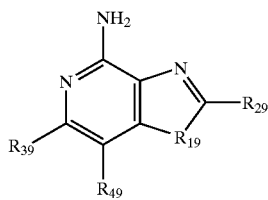

wherein:
$R_{19}$ is selected from the group consisting of oxygen, sulfur and selenium;
$R_{29}$ is selected from the group consisting of
- -hydrogen;
- -alkyl;
- -alkyl-OH;
- -haloalkyl;
- -alkenyl;
- -alkyl-X-alkyl;
- -alkyl-X-alkenyl;
- -alkenyl-X-alkyl;
- -alkenyl-X-alkenyl;
- -alkyl-N($R_{59}$)$_2$;
- -alkyl-N$_3$;
- -alkyl-O-C(O)-N($R_{59}$)$_2$;
- -heterocyclyl;
- -alkyl-X-heterocyclyl;
- -alkenyl-X-heterocyclyl;
- -aryl;
- -alkyl-X-aryl;
- -alkenyl-X-aryl;
- -heteroaryl;
- -alkyl-X-heteroaryl; and
- -alkenyl-X-heteroaryl;

$R_{39}$ and $R_{49}$ are each independently:
- -hydrogen;
- -X-alkyl;
- -halo;
- -haloalkyl;
- -N($R_{59}$)$_2$;
- or when taken together, $R_{39}$ and $R_{49}$ form a fused aromatic, heteroaromatic, cycloalkyl or heterocyclic ring;

X is selected from the group consisting of —O—, —S—, —NR$_{59}$—, —C(O)—, —C(O)O—, —OC(O)—, and a bond; and each $R_{59}$ is independently H or $C_{1-8}$alkyl;

Suitable imidazonaphthyridine and tetrahydroimidazomaphthyridine IRM compounds are those of Formulae X and XI below:

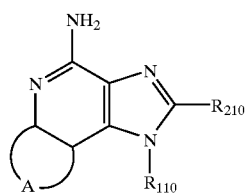

wherein
A is =N—CR=CR—CR=; =CR—N=CR—CR=; =CR—CR=N—CR=; or =CR—CR=CR—N=;

$R_{110}$ is selected from the group consisting of:
- -hydrogen;
- —$C_{1-20}$alkyl or $C_{2-20}$alkenyl that is unsubstituted or substituted by one or more substituents selected from the group consisting of:
  - -aryl;
  - -heteroaryl;
  - -heterocyclyl;
  - —O—$C_{1-20}$alkyl,
  - —O—($C_{1-20}$alkyl)$_{0-1}$-aryl;
  - —O—($C_{1-20}$alkyl)$_{0-1}$-heteroaryl;
  - —O—($C_{1-20}$alkyl)$_{0-1}$-heterocyclyl;
  - —$C_{1-20}$alkoxycarbonyl;
  - —S(O)$_{0-2}$-$C_{1-20}$alkyl;
  - —S(O)$_{0-2}$-($C_{1-20}$alkyl)$_{0-1}$-aryl;
  - —S(O)$_{0-2}$-($C_{1-20}$alkyl)$_{0-1}$-heteroaryl;
  - —S(O)$_{0-2}$-($C_{1-20}$alkyl)$_{0-1}$-heterocyclyl;
  - —N($R_{310}$)$_2$;
  - —N$_3$;
  - oxo;
  - -halogen;
  - —NO$_2$;
  - —OH; and
  - —SH; and
- —$C_{1-20}$alkyl-NR$_{310}$—Q—X—$R_{410}$ or —$C_{2-20}$alkenyl-NR$_{310}$—Q—X—$R_{410}$ wherein Q is —CO— or —SO$_2$—; X is a bond, —O— or —NR$_{310}$— and $R_{410}$ is aryl; heteroaryl; heterocyclyl; or —$C_{1-20}$alkyl or $C_{2-20}$alkenyl that is unsubstituted or substituted by one or more substituents selected from the group consisting of:
  - -aryl;
  - -heteroaryl;
  - -heterocyclyl;
  - —O—$C_{1-20}$alkyl,
  - —O—($C_{1-20}$alkyl)$_{0-1}$-aryl;
  - —O—($C_{1-20}$alkyl)$_{0-1}$-heteroaryl;
  - —O—($C_{1-20}$alkyl)$_{0-1}$-heterocyclyl;
  - —$C_{1-20}$alkoxycarbonyl;
  - —S(O)$_{0-2}$—$C_{1-20}$alkyl;
  - —S(O)$_{0-2}$—($C_{1-20}$alkyl)$_{0-1}$-aryl;
  - —S(O)$_{0-2}$—($C_{1-20}$alkyl)$_{0-1}$-heteroaryl;
  - —S(O)$_{0-2}$—($C_{1-20}$alkyl)$_{0-1}$-heterocyclyl;
  - —N($R_{310}$)$_2$;
  - —NR$_{310}$—CO—O—$C_{1-20}$alkyl;
  - —N$_3$;
  - oxo;
  - -halogen;
  - —NO$_2$;
  - —OH; and
  - —SH; or $R_{410}$ is

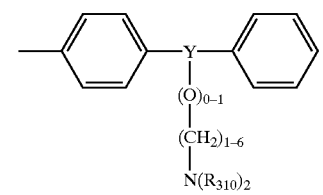

wherein Y is —N— or —CR—;

$R_{210}$ is selected from the group consisting of:
- -hydrogen;
- —$C_{1-10}$alkyl;
- —$C_{2-10}$alkenyl;
- -aryl;

—$C_{1-10}$alkyl-O—$C_{1-10}$-alkyl;
—$C_{1-10}$alkyl-O—$C_{2-10}$alkenyl; and
—$C_{1-10}$alkyl or $C_{2-10}$alkenyl substituted by one or more substituents selected from the group consisting of:
—OH;
-halogen;
—$N(R_{310})_2$;
—CO—$N(R_{310})_2$;
—CO—$C_{1-10}$alkyl;
—$N_3$;
-aryl;
-heteroaryl;
-heterocyclyl;
—CO-aryl; and
—CO-heteroaryl;
each $R_{310}$ is independently selected from the group consisting of hydrogen and $C_{1-10}$alkyl; and
each R is independently selected from the group consisting of hydrogen,
$C_{1-10}$alkyl, $C_{1-10}$alkoxy, halogen and trifluoromethyl,
or a pharmaceutically acceptable salt thereof.

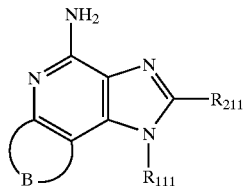

XI wherein
B is —NR—$C(R)_2$—$C(R)_2$—$C(R)_2$—; —$C(R)_2$—NR—$C(R)_2$—$C(R)_2$—;
—$C(R)_2$—$C(R)_2$—NR—$C(R)_2$— or —$C(R)_2$—$C(R)_2$—$C(R)_2$—NR—;
$R_{111}$ is selected from the group consisting of:
-hydrogen;
—$C_{1-20}$alkyl or $C_{2-20}$alkenyl that is unsubstituted or substituted by one or more substituents selected from the group consisting of:
-aryl;
-heteroaryl;
-heterocyclyl;
—O—$C_{1-20}$alkyl;
—O—$(C_{1-20}$alkyl$)_{0-1}$-aryl;
—O—$(C_{1-20}$alkyl$)_{0-1}$-heteroaryl;
—O—$(C_{1-20}$alkyl$)_{0-1}$-heterocyclyl;
—$C_{1-20}$alkoxycarbonyl;
—$S(O)_{0-2}$—$C_{1-20}$alkyl;
—$S(O)_{0-2}$—$(C_{1-20}$alkyl$)_{0-1}$-aryl;
—$S(O)_{0-2}$—$(C_{1-20}$alkyl$)_{0-1}$-heteroaryl;
—$S(O)_{0-2}$—$(C_{1-20}$alkyl$)_{0-1}$-heterocyclyl;
—$N(R_{311})_2$;
—$N_3$;
oxo;
-halogen;
—$NO_2$;
—OH; and
—SH; and
—$C_{1-20}$alkyl-$NR_{311}$—Q—X—$R_{411}$ or —$C_{2-20}$alkenyl-$NR_{311}$—Q—X—$R_{411}$ wherein Q is —CO— or —$SO_2$—; X is a bond, —O— or —$NR_{311}$— and $R_{411}$ is aryl; heteroaryl; heterocyclyl; or —$C_{1-20}$alkyl or $C_{2-20}$alkenyl that is unsubstituted or substituted by one or more substituents selected from the group consisting of:
-aryl;
-heteroaryl;
-heterocyclyl;
—O—$C_{1-20}$alkyl,
—O—$(C_{1-20}$alkyl$)_{0-1}$-aryl;
—O—$(C_{1-20}$alkyl$)_{0-1}$-heteroaryl;
—O—$(C_{1-20}$alkyl$)_{0-1}$-heterocyclyl;
—$C_{1-20}$alkoxycarbonyl;
—$S(O)_{0-2}$-$C_{1-20}$alkyl;
—$S(O)_{0-2}$-$(C_{1-20}$alkyl$)_{0-1}$-aryl;
—$S(O)_{0-2}$-$(C_{1-20}$alkyl$)_{0-1}$-heteroaryl;
—$S(O)_{0-2}$-$(C_{1-20}$alkyl$)_{0-1}$-heterocyclyl;
—$N(R_{311})_2$;
—$NR_{311}$—CO—O—$C_{1-20}$alkyl;
—$N_3$;
oxo;
-halogen;
—$NO_2$;
—OH; and
—SH; or $R_{411}$ is

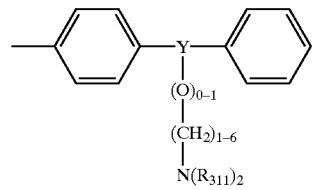

wherein Y is —N— or —CR—;
$R_{211}$ is selected from the group consisting of:
-hydrogen;
—$C_{1-10}$alkyl;
—$C_{2-10}$alkenyl;
-aryl
—$C_{1-10}$alkyl-O—$C_{1-10}$-alkyl;
—$C_{1-10}$alkyl-O—$C_{2-10}$alkenyl; and
—$C_{1-10}$alkyl or $C_{2-10}$alkenyl substituted by one or more substituents selected from the group consisting of:
—OH;
-halogen;
—$N(R_{311})_2$;
—CO—$N(R_{311})_2$;
—CO—$C_{1-10}$alkyl;
—$N_3$;
-aryl;
-heteroaryl;
-heterocyclyl;
—CO-aryl; and
—CO-heteroaryl;
each $R_{311}$ is independently selected from the group consisting of hydrogen and $C_{1-10}$alkyl; and
each R is independently selected from the group consisting of hydrogen, $C_{1-10}$alkyl, $C_{1-10}$alkoxy, halogen and trifluoromethyl, and pharmaceutically acceptable salts thereof.

The compounds recited above are disclosed in the patents and applications noted above in the background, all of which are incorporated herein by reference.

The substituents $R_{11}$-$R_{111}$ above are generally designated "1-substituents" herein. The preferred 1-substituents are alkyl containing one to six carbon atoms and hydroxyalkyl containing one to six carbon atoms. Optionally, the 1-substituent is 2-methylpropyl or 2-hydroxy-2-methylpropyl.

The substituents $R_{21}$-$R_{211}$ above are generally designated "2-substituents" herein. Optional 2-substituents are hydrogen, alkyl of one to six carbon atoms, alkoxyalkyl wherein the alkoxy moiety contains one to four carbon atoms and the alkyl moiety contains one to four carbon atoms, and hydroxyalkyl of one to four carbon atoms. Optionally, the 2-substituent is hydrogen, methyl, butyl, propyl hydroxymethyl, ethoxymethyl or methoxyethyl.

In instances where n can be zero, one, or two, n is preferably zero or one.

IRM Pharmaceutical Formulations

The amount of an IRM compound that will be therapeutically effective in a specific situation will depend on such things as the activity of the particular compound, the mode of administration, the particular formulation and the condition being treated. As such, it is not practical to identify specific administration amounts herein; however, those skilled in the art will be able to determine appropriate therapeutically effective amounts based on the guidance provided herein, information available in the art pertaining to these compounds, and routine testing.

The pharmaceutical formulations described below can be used for topical administration of an IRM. Many of the formulations provided are particularly advantageous for topical administration to a mucosal surface. In some embodiments, the formulations can affect the pharmacokinetics of the IRM such that reduced concentrations of the IRM provide similar pharmacodynamic affects as that of other formulations having a greater IRM concentration.

Generally, a pharmaceutical formulation of the invention includes an IRM, a fatty acid, a preservative system and an optional viscosity enhancing agent such as a carbomer. The IRMs can be prepared using methods previously described in the patents listed in the background section above as well as U.S. Pat. Nos. 4,988,815; 5,367,076; 5,175,296; 5,395,937; and 5,741,908, the disclosures which are incorporated herein by reference. Unless otherwise specified, all percentages are weight percentages based on the total composition weight.

The amount of an IRM present in a pharmaceutical formulation of the invention will be an amount effective to treat a targeted condition, to prevent recurrence of the condition, or to promote immunity against the condition. The amount of IRM is preferably about 0.1% to about 9% by weight based on the total formulation weight. Optionally, the IRM amount does not exceed about 5% by weight and most preferably is about 0.1 to about 3% by weight for mucosal surface applications.

Typically, a pharmaceutical formulation of the invention is an oil in water emulsion. The oil component of the formulation includes an IRM and a fatty acid. The fatty acid is present in the formulation in an amount sufficient to solubilize the IRM. This is generally about 2% to about 45%, typically about 10% to about 30%, and preferably about 15% to about 18% based on the total weight of the formulation. Fatty acids such as isostearic acid are suitable for the formulations. Alternatively, the IRM can be solubilized in linear chain carboxylic acids of six to eight carbon atoms.

A pharmaceutical formulation of the invention can also include an emulsifier such as a non-ionic surfactant. Suitable surfactants include, for example, polysorbate 60, sorbitan monostearate, polyglyceryl-4 oleate, polyoxyethylene(4) lauryl ether, etc. For some formulations, surfactants such as Poloxamers (e.g., Pluronic F68 available from BASF, Ludwigschafen, Germany) and sorbitan trioleate (e.g., Span 85 available from Sigma Chemical Co., St. Louis, Mo.), alone or in combination, are preferred. The non-ionic surfactant is typically present in an amount of about 0.5% to about 10% of total formulation weight. In preferred embodiments, the total emulsifier content does not exceed about 5% of total formulation weight, and is more preferably about 3.5% of total formulation weight.

A formulation of the invention can also include a viscosity enhancing agent such as a carbomer, preferably having mucoadhesive properties. The carbomer can be present in an amount of about 0.1% to about 8%, preferably about 0.5% to about 4%, more preferably about 0.5 to about 3%, and most preferably about 1.0% of total formulation weight. Suitable carbomers include polyacrylic acids such as Carbopol 934P, Carbopol 971P, Carbopol 940 and Carbopol 974P available from B.F. Goodrich. A preferred carbomer is Carbopol 974P.

In some optional embodiments, the formulation can also include a chelating agent. The chelating agent functions to chelate metal ions. If present, unchelated metal ions can suppress gel formation by suppressing ionization which facilitates gel formation in a carbomer containing formulation. An optional chelating agent is disodium ethylenediaminetetraacetate (EDTA) in a concentration of about 0.0001 to about 0.5%, typically about 0.0005 to about 0.1% per total formulation weight.

A preservative such as methylparaben, sorbic acid, propylene glycol, etc. can also be added. In one optional embodiment, methylparaben and sorbic acid are each provided at concentrations of about 0.05% to about 0.3%, preferably about 0.15% of total formulation weight and propylene glycol is present in amounts up to about 30%, preferably about 5%. It was discovered that this combination of preservatives advantageously meets the Preservation Effectiveness Test (PET), 1997 European Pharmacopeia, Test 5.1.3 Efficacy Antimicrobial Preservation—Topical Preparations—A Criteria. This renders the formulation suitable for use in a multi-dose dispenser without adversely affecting the stability of the formulation. The methylparaben and sorbic acid can be solubilized in propylene glycol prior to adding to the formulation.

The remainder of the pharmaceutical formulation can be comprised of water to provide a formulation that can be washed away from the mucosal surface by normal physiological clearing mechanisms.

In addition to providing mucoadhesive properties to the formulation, the carbomer also increases viscosity by forming a stabilizing gel. Many factors, such as the amount of oil phase, the drug load, and the amount of carbomer used will affect the pH at which gelation occurs. In some formulations, the presence of metal ions and surfactants increases the pH at which the carbomer will form a gel. Thus, in the absence of a chelating agent, or in the presence of increased surfactant levels, the pH at which the carbomer will gel can be increased. Thus it may be necessary to add an organic or inorganic base or other substance to facilitate gel formation. Suitable inorganic bases include, for example, KOH, NaOH, etc. The pH for a pharmaceutical formulation of the invention is typically about pH 3.0 to about pH 7.0, preferably about pH 4.0 to about pH 6.0.

Mucosal Surface Applications

According to the invention, the compositions can be applied topically, particularly to non-cornified epithelial surfaces such as mucosal surfaces. Mucosal surfaces include mucosal membranes such as buccal, gingival, nasal, tracheal, bronchial, gastrointestinal, rectal, urethral, ureteral, vaginal, cervical, uterine, etc. Depending on the IRM concentration, formulation composition, and mucosal surface, the therapeutic affect of the IRM may extend only to the superficial layers of the mucosal surface or to tissues deep to the surface.

In one embodiment, the disclosed IRMs can be topically applied to the vaginal or supravaginal region of the cervix for treatment of dysplastic conditions such as cervical intraepithelial neoplasia. In some embodiments, the above described formulations are particularly advantageous for cervical application of an IRM for a period of time sufficient to obtain a desired therapeutic effect without undesired systemic absorption of the IRM.

Cervical Intraepithelial Neoplasia (CIN)

Approximately 16,000 new cases of invasive cancer of the cervix are diagnosed each year in the U.S. despite extensive screening of women to detect predictive cellular changes. There are also about 3,000 deaths due to cervical cancer in the U.S. alone and this is usually secondary to not detecting the primary cancerous lesion in a timely manner.

The Papanicoulaou Test (Pap smear) is the screening test which has been accepted since the 1950s as the method to detect abnormal cells of the cervix, including inflammation and dysplasia, which includes cervical cancer. This screening test has been widely adopted in industrialized countries and has had a profound impact on mortality associated with cervical cancers. An abnormal Pap smear prompts close observation for disease progression with the potential for the therapeutic interventions of destruction or excision of cancerous or pre-cancerous tissues. These excisional treatments are expensive, uncomfortable and associated with failure rates which range from 2 to 23% and with higher failure rates reported for the more advanced lesions. Failure rates have recently been documented to approximate 10% following laser treatment.

The etiologic agent for cervical cancer was originally thought to be the herpes virus. However, there was a gradual shift from this focus on herpes virus to the human papillomavirus (HPV) when it was shown that the cytopathic effects of HPV in experimental systems very closely mimicked what was seen in human disease. Improved experimental methods over the recent past have allowed the characterization of a full spectrum of HPV subtypes, which has resulted in the conclusion that the high risk HPV types (e.g., HPV 16, 18, and less frequently 31, 33, 35, 45) are very likely the exclusive initiating factor (i.e., oncogenic agent) for cervical dysplasia and subsequent cancers. The mechanism of HPV transformation of the normal cell to a dysplastic cell is associated with the HPV encoded oncoproteins (E6 and E7) from the high risk genotypes binding the cell's tumor suppressor gene products p53 and Rb resulting in disruption of the cell cycle control mechanism in which p53 and Rb play an important role. In addition, the application of these molecular methods has resulted in the epidemilogic observation that HPV is isolated from approximately 93% of cervical tumors, which has further strengthened the generally accepted conclusion that HPV infection is the most important initiating agent for cervical cancer.

Exposure to HPV is common in sexually active women, but it does not invariably lead to dysplasia or cancer in most of the exposed women. Infected women who harbor persistent viral DNA have about five times the chance of persistent dysplasia compared to women who are able to eradicate the virus. The importance of cell-mediated immune (CMI) response to HPV infection is illustrated by the observation that the antibody mediated immune response is not effective in eliminating established infections as is demonstrated by the fact that patients with invasive cervical dancer often exhibit high antibody levels against the viral E6 and E7 proteins. This particular antibody response probably reflects extensive antigen exposure in the face of increasing tumor burden. In contrast to the apparently inconsequential effect of the humoral immune response, the cell-mediated immune response (Th-1-Type Response) appears to be effective in controlling tumor progression. Regression of intraepithelial lesions is accompanied by a cellular infiltrate consisting of CD4$^+$ T-CELLS, CD8$^+$ T-CELLS, natural killer cells (NK) and macrophages. This inflammatory infiltrate was usually associated with tumor regression which is in contrast to women who lack the ability to mount this inflammatory response and who experience disease progression. In addition, patients with a defect in cell-mediated immunity have increased cervical cancer rates, whereas those with defects in the production of antibody do not exhibit the same susceptibility.

In one optional embodiment, the inventors foresee the topical application of IRMs for the non-invasive treatment of cervical conditions including cervical intraepithelial neoplasia (CIN).

Intravaginal Applicators for an IRM

To obtain a beneficial therapeutic or prophylactic effect for a cervical condition, intravaginal application of a herein disclosed IRM is preferred. The IRM can be applied via a dosing formulation or dispenser which ensures contact of the IRM with the mucosal surface of the cervix for a period of time sufficient to provide the desired therapeutic effect. Any of the dispensers (i.e., applicators) described herein and/or shown in the drawings could be used to apply the IRM.

In addition to the applicators already described, an IRM can be formulated as a suppository and administered intravaginally using a suppository applicator. A suitable suppository applicator includes known cardboard tube applicators for dispensing medications to the vaginal cavity. Formulations according to the invention can also be administered using a barrel type applicator, such as those described herein and/or shown in the drawings. An example of a suitable barrel type applicator can be found in U.S. Pat. No. 5,282,789, the disclosure of which is incorporated herein by reference.

In optional embodiment, an IRM can be administered directly to the cervical mucosa. In one such embodiment, the IRM can be topically applied to the cervical mucosa by using a direct cervical applicator, as previously described or using a cervical cap. One example of a suitable cervical cap is found in U.S. Pat. No. 4,858,624, the disclosure of which is incorporated herein by reference. Suitable IRM formulations for direct cervical applications are disclosed above and in the Examples below. In general, an IRM formulated pursuant to any of formulations A—J in the Examples below can be placed into the concave region of the cervical cap which is then applied directly over the cervix. These formulations might also be applied with other types of applicator devices including those shown in the drawings and described herein. Optionally, the IRM is formulated to include a viscosity agent, such as a carbomer, to enhance the residence time of the IRM on the cervix.

The following Examples are provided to further describe IRM formulations and methods according to the invention. The examples, however, are not intended to limit the formulations and methods.

EXAMPLES

Example 1

Evaluation of the Safety, Pharmacokinetics (PK) and Pharmacodynamics (PD) OF 1-(2-Methylpropyl)-1H-imadazo[4,5-C]quinolin-4-amine (imiquimod) Applied to the Cervix Methods This was a single dose, randomized, double-blind, placebo controlled dose escalation study which evaluated five doses of imiquimod. 50, 100, 150, 200 and 250 mg of imiquimod in a cream formulation were applied to the cervix for eight hours. The ingredients of the formulation of the imiquimod cream used for this study (Formulation A) is presented in Table I below. Each dose group was composed of 8 subjects (6 active and 2 placebo), with two subjects treated as dose leaders, and the remaining six subjects were treated after an acceptable response by the dose leaders. Safety was assessed by adverse events (AE's), laboratory tests, and colposcopy with photodocumentation of the cervix at pre-dose and 24 hours post-dose, and 48 hours post-dose if required. Systemic exposure (PK) was determined by measuring imiquimod and metabolites through 48 hours post-dose and the PD response was determined by serum analysis for the cytokines: tumor necrosis factor-α (TNF-α), interferon-α (IFN-α), interleukin-1 receptor agonist (IL-1RA), interleukin-6 (IL-6), neopterin (NPT) and 2'5' oligoadenlyate synthetase (2'5' AS) during dosing and selected times during the 48 hours post-dose. Statistical tests to evaluate AE's and demographics, laboratory tests, vital signs and ECG's were Fisher's Exact, Wilcoxon Rank-Sum and Kruskall Wallis Tests respectively. Cytokine changes between dose groups were compared using Wilcoxon Rank-Sum and changes from baseline were evaluated using Spearman Rank Correlation.

Results

Thirty-nine generally healthy, surgically sterilized, 18–50 year-old females within 25% of ideal body weight were included in the study. All women had normal baseline colposcopy results with normal and borderline dyskariosis on cervical histology. AE's were reported in each of the 39 subjects with mild temperature elevation the most common event (92%). There were no differences among groups with respect to subjects who experienced one or more events, or in AE's attributed as possibly or probably related to drug. (Two serious AE's occurred which were intercurrent events associated with a fractured ankle and its surgical repair.) There were statistically significant changes in some laboratory parameters and pulse rates that were not considered clinically significant. There were no differences in ECG's or physical exams. Pelvic and colposcopic examinations revealed few reactions with 2 of 6 receiving 250 mg experiencing cervical changes of minor small vesicles or smaller ulcer. These reactions resolved within 48 hours. No quantifiable (>5 ng/ml) serum levels of imiquimod were detected. Significant changes from baseline were seen in IFN and IL-6 in the 250 mg group and in NPT. 2'5' AS and IL-1RA in the 150 mg, 200 mg, and 250 mg groups.

The study showed that single doses of imiquimod up to 250 mg applied to the cervix for 8 hours in healthy volunteers is safe with minimal systemic exposure. Cervical application of a dose ≧150 mg increases the systemic concentration of certain cytokines.

TABLE 1

| Components | Formulation A (% w/w) |
| --- | --- |
| Imiquimod | 5.0 |
| Isostearic Acid | 25.0 |
| Benzyl Alcohol | 2.0 |
| Cetyl Alcohol | 2.2 |
| Stearyl Alcohol | 3.1 |
| White Petrolatum | 3.0 |
| Polysorbate 60 | 3.4 |
| Sorbitan Monostearate | 0.6 |
| Glycerin | 2.0 |
| Methyl Paraben | 0.2 |
| Propyl Paraben | 0.02 |
| Water | 52.98 |

TABLE 1-continued

| Components | Formulation A (% w/w) |
| --- | --- |
| Xanthan Gum | 0.5 |
| PH | 5.1 |
| Viscosity (cps) | $0.33 \times 10^5$ |

Example 2

Preparation of Pharmaceutical Formulation B

This example describes a novel formulation for a vaginal application, that is a stable formulation, with a high viscosity, and well preserved to pass the EP preservative effectiveness test (PET) criteria. The w/w % of ingredients of this formulation (Formulation B) are shown in Table 2 below.

Imiquimod was dissolved in isostearic acid with Span 85. Pluronic F68, EDTA, Carbopol 974P, propylene glycol, sorbic acid, and methylparaben were dissolved in water. After emulsification to form an oil-in-water emulsion, sodium hydroxide was added to achieve a pH of about 5.2. The pH range for this formulation can be about 4.8 to 6.0.

TABLE 2

| Components | Formulation B (% w/w) |
| --- | --- |
| Imiquimod | 5 |
| Isostearic acid | 28 |
| Pluronic F68 | 2.98 |
| Purified water | 43.78 |
| Carbopol 974P | 1.7 |
| Disodium EDTA | 0.05 |
| Propylene glycol | 15 |
| Sorbic acid | 0.15 |
| Methylparaben | 0.15 |
| Span 85 | 2.02 |
| 5N NaOH | 1.17 |
| PH | 5.1 |
| Viscosity (cps) | $6.4 \times 10^5$ |

Example 3

Preparation of Pharmaceutical Formulations C–F

Pharmaceutical Formulations C–F were prepared with the components recited below in Table 3. The method for preparing Formulations C–F was the same as that disclosed for preparing Formulation B in Example 2.

TABLE 3

| Components | Formulation C (% w/w) | Formulation D (% w/w) | Formulation E (% w/w) | Formulation F (% w/w) |
| --- | --- | --- | --- | --- |
| Imiquimod | 1.0 | 1.0 | 3.0 | 3.0 |
| Isostearic acid | 5.6 | 28.0 | 16.8 | 28.0 |
| Pluronic F68 | 1.79 | 1.79 | 1.79 | 1.79 |
| Purified water | 69.05 | 48.30 | 56.25 | 46.75 |
| Carbopol 974P | 2.8 | 2.10 | 2.5 | 1.80 |
| Disodium EDTA | 0.05 | 0.05 | 0.05 | 0.05 |
| PG* | 15.0 | 15.0 | 15.0 | 15.0 |
| Sorbic acid | 0.15 | 0.15 | 0.15 | 0.15 |
| Methylparaben | 0.15 | 0.15 | 0.15 | 0.15 |
| Span 85 | 1.21 | 1.21 | 1.21 | 1.21 |
| 5N NaOH | 3.2 | 2.26 | 3.1 | 2.1 |
| pH | 5.1 | 5.2 | 5.2 | 5.3 |
| Viscosity (cps) | $5.8 \times 10^5$ | $8.8 \times 10^5$ | $11.0 \times 10^5$ | $10.0 \times 10^5$ |

*PG is Propylene glycol

Example 4
Imiquimod Transport Across Hairless Mouse Skin from Two Formulations A and B, Both at 5% W/W Imiquimod.

Figure 16:
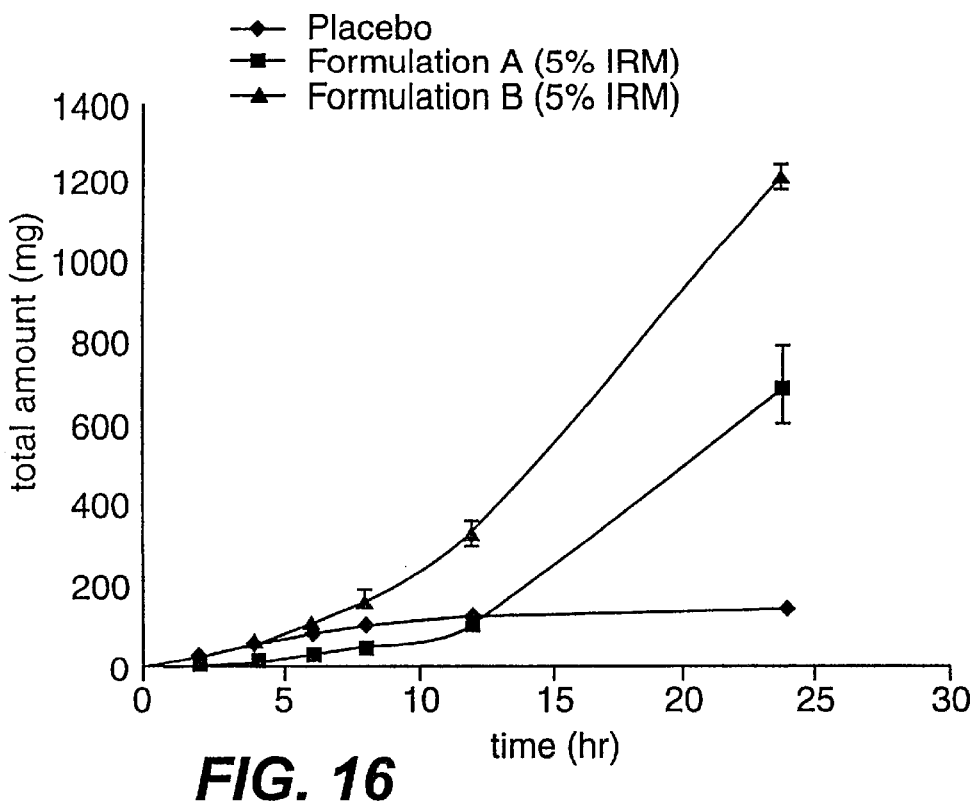
FIG. 16 is a graph comparing imiquimod transport across hairless mouse skin from three pharmaceutical formulations each containing 5% imiquimod.

FIG. 16 is a graph of the results of imiquimod penetration studies of Formulations A and B, of Examples 1 and 2, using hairless mouse skin according to the procedure described in U.S. Pat. No. 5,238,944, the entire disclosure of which is incorporated herein by reference.

In brief, hairless mouse skin was removed from female hairless mice that were 5 to 7 weeks old (available from Charles River). The skin was maintained on ice until used. The mouse skin was mounted on a diffusion cell of the type shown in U.S. Pat. No. 5,238,944. The mouse skin was mounted with the epidermal side up between upper and lower portions of the cell which are held together by means of ball joint clamp.

The portion of the cell below the mounted skin was completely filled with 0.1 N HCl receptor fluid such that the receptor fluid contacted the skin. The receptor fluid was stirred using a magnetic stir bar and a magnetic stirrer.

Approximately $100 \pm 5$ mg formulation to be tested was applied to the epidermal (upper) side of the skin to cover in an even layer only the area of skin that would be in contact with the receptor fluid when the skin was mounted in the diffusion cell. The formulations were applied to the skin prior to the time the receptor fluid was added to the cell below the skin.

The cell was then placed in a constant temperature (31° C.) chamber. To maintain constant temperature, the chamber utilized a heat exchanger coupled to a constant temperature bath, with a fan to circulate air. The receptor fluid was stirred by means of a magnetic stirring bar throughout the experiment to ensure a uniform sample and a reduced diffusion barrier layer on the dermal side of the skin. At specified time intervals (1, 2, 4, 6, 8, 12 and 24 hours), the entire volume of receptor fluid was removed and immediately replaced with fresh receptor fluid. The withdrawn receptor fluid was analyzed for imiquimod content by conventional high pressure chromatography as follows:

Detector: UV at 258 nm; Mobile Phase: 25/75 acetonitrile/water containing 1% triethylamine, 0.2% 1-octane sulfonate with the pH adjusted to 2.0 with $H_3PO_4$; Stationary Phase: C8 Zorbax RX-C8 5μ; Flow Rate: 2 ml/min; Run Time: approximately 10 minutes.

Cumulative amount of penetration was plotted versus time to obtain the steady state rate.

Example 5
Imiquimod Transport Across Nude Skin from Formulations C–F at 1% W/W and 3% W/W Imiquimod with Varied Concentrations of Isostearic Acid (ISA)

Table 4 below provides the imiquimod concentration, isostearic acid concentration, viscosity, pH and steady state rate (μg/hour) of Formulations C–F across nude mouse skin.

Figure 17:
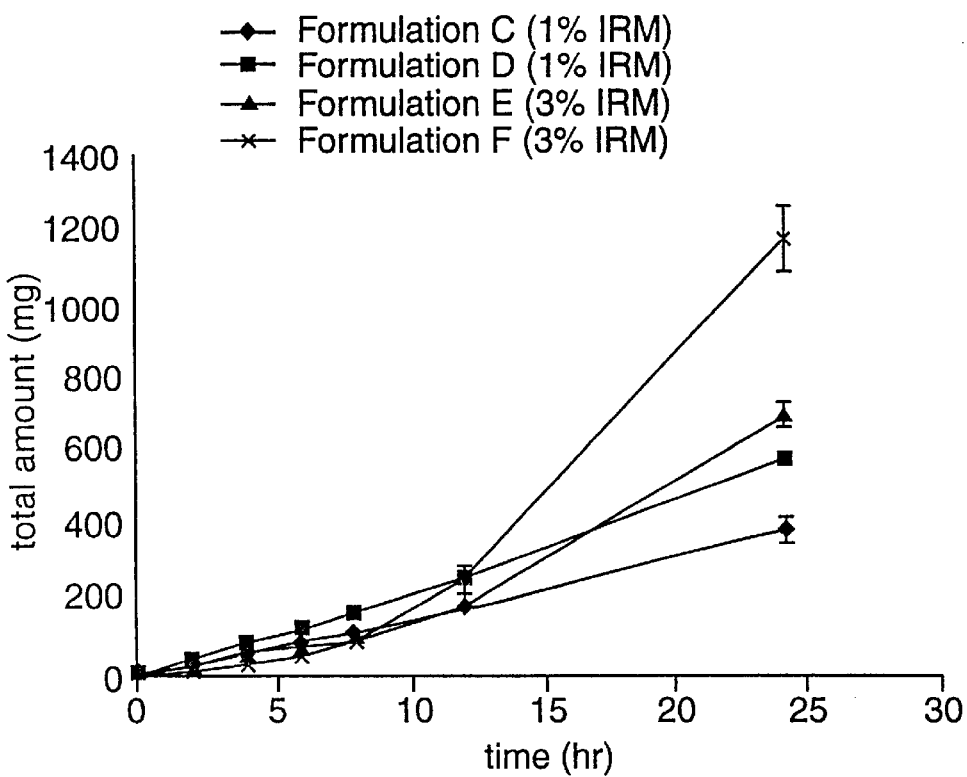
FIG. 17 is a graph comparing imiquimod transport across hairless mouse skin from four pharmaceutical formulations containing varied concentrations of imiquimod and isostearic acid.

The results are graphed in FIG. 17. The procedure used to study skin penetration was the same as that disclosed in Example 4.

TABLE 4

| Formulation | IRM Concentration (% w/w) | ISA Concentration (% w/w) | Viscosity (×10⁻⁵ cps) | Steady State Rate (μg/hr) |
|---|---|---|---|---|
| C | 1% | 5.6% | 5.8 | 18.1 |
| D | 1% | 28% | 8.8 | 26.1 |
| E | 3% | 16.8% | 11 | 39.9 |
| F | 3% | 28% | 10 | 71.5 |

Example 6
Pharmacokinetics Comparison of Imiquimod in Rats after Single Dose Vaginal Application of Formulation A and Formulation B Serum imiquimod concentration versus time profiles were compared in ovariectomized rats after single intravaginal doses of Formulation A or Formulation B. The two 5% w/w formulations were dosed to provide a dose level of 35 mg/kg. After dosing, each rat was collared to prevent removal of the formulation by licking. After about six hours, the vagina was lavaged and the collars removed. Blood samples were collected at pre-dose and at 0.5, 1, 2, 3, 4 and 24 hours post-dose. Due to the higher viscosity of Formulation B, intravaginal administration to the rats was considerably easier and retention of Formulation B was superior to Formulation A.

Figure 18:
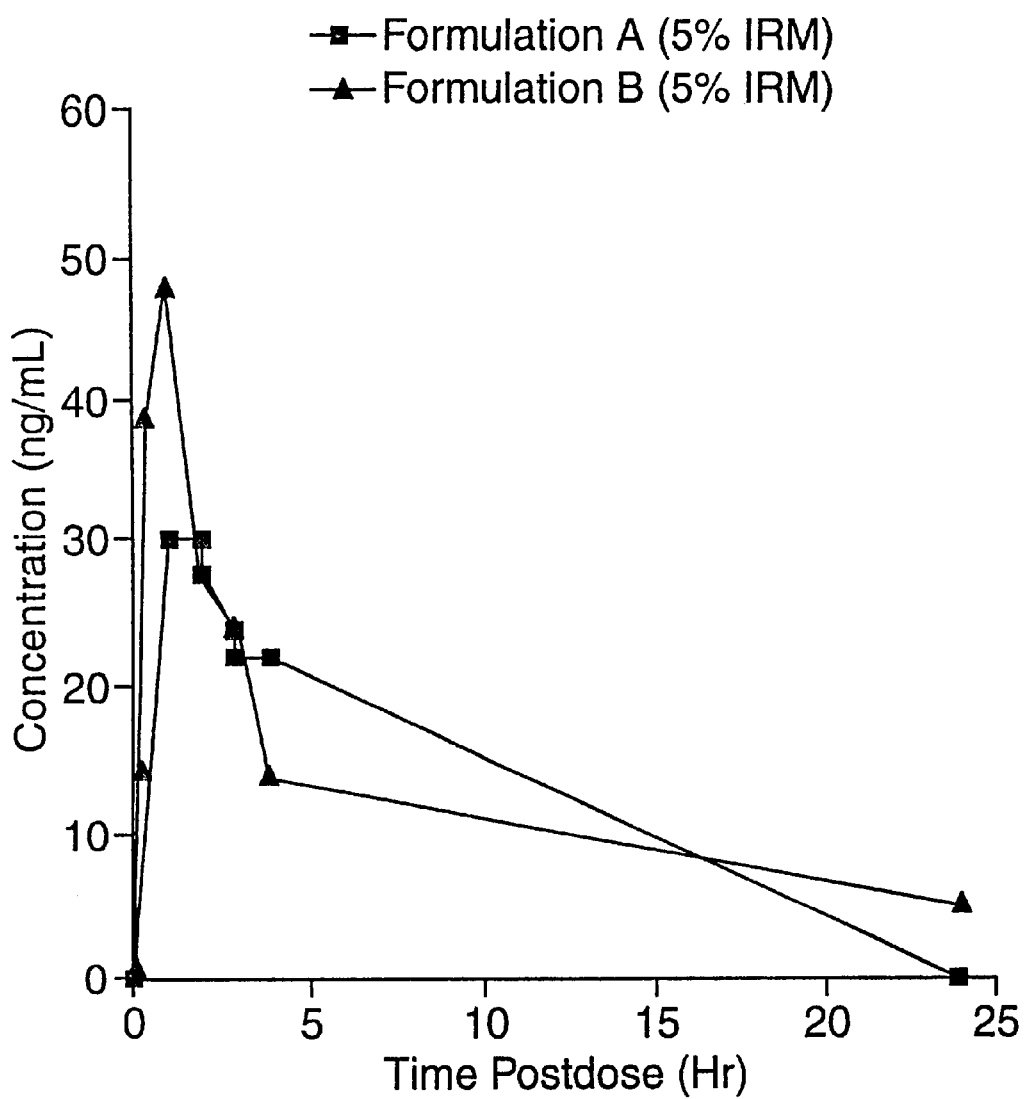
FIG. 18 is a graph comparing mean serum imiquimod concentration in rats after a single intravaginal dose of Formulation A or Formulation B.
Figure 19A:
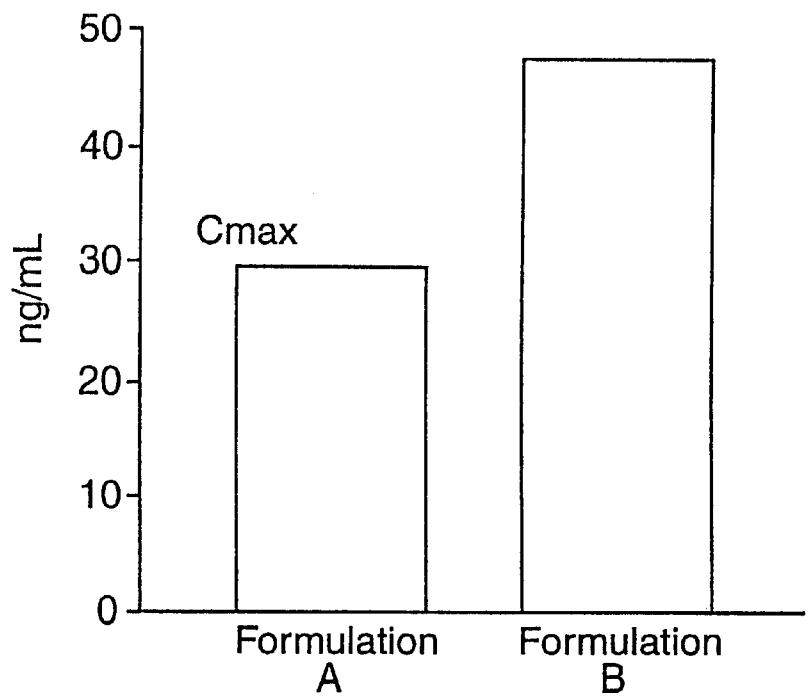
FIGS. 19A and 19B provide bar graphs of the pharmacokinetic comparison of imiquimod in rats after vaginal dosing of Formulation A or Formulation B.
Figure 19B:
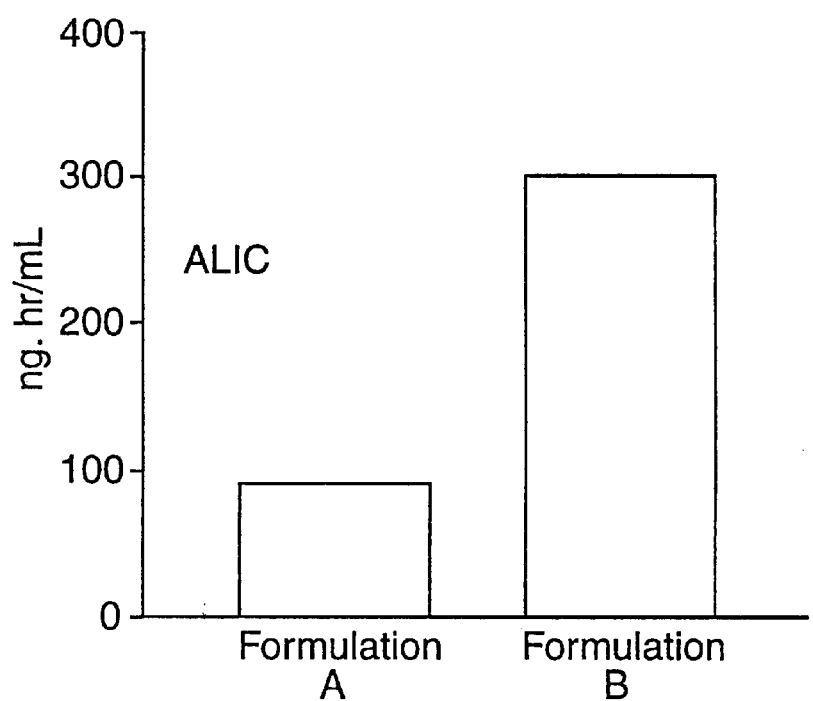

Serum was analyzed by HPLC for imiquimod. Mean serum imiquimod concentrations versus time are depicted in FIG. 18. The time to achieve maximum serum concentrations of imiquimod ($T_{max}$) was similar (1 hr) for both formulations. However, the maximum imiquimod concentration ($C_{max}$) for Formulation B was approximately 1.6 times greater than for Formulation A and the respective area under the curve versus time (AUC) was 3.3 times greater (FIGS. 19A and 19B). Based upon these data, the rate and extent of absorption of imiquimod was greater from Formulation B than from Formulation A.

Example 7
Preparation of Pharmaceutical Formulation G

The w/w % of the ingredients for Formulation G are shown in Table 5.

An oil phase was prepared as follows. Imiquimod (20.0 g) was slowly added with stirring to isostearic acid (3000 g). The mixture was stirred and heated, as necessary, up to 55° C. to facilitate dissolution of the imiquimod. After dissolution was complete the heat was turned off. Sorbitan trioleate (200 g) was added and thoroughly mixed. Carbomer 974 was slowly added with mixing. The mixing was continued until the carbomer was uniformly dispersed in the oil phase. The oil phase was then allowed to cool to a temperature of less than 30° C.

An aqueous phase was prepared as follows. Sorbic acid (30.0 g) and methylparaben (40.0 g) were added with stirring to propylene glycol (1000 g). The resulting mixture was stirred and heated gently (<45° C.) until a solution was obtained. The heat source was removed. Polaxamer 188 (500 g) was added to the solution. The resulting mixture was stirred until the polaxamer was thoroughly wet. The resulting slurry was then added to a solution of edetate disodium (10.0 g) in purified water (13950 g). The resulting mixture was stirred until a clear solution was obtained.

A sodium hydroxide solution was prepared by dissolving sodium hydroxide pellets (50 g) in purified water (1000 g).

The oil phase was added to the aqueous phase and then the sodium hydroxide solution was added. The resulting mixture was mixed for a minimum of 30 minutes until a smooth and shiny cream was obtained. The pH was determined and adjusted, if necessary, to 5.6–5.8 with sodium hydroxide solution.

Example 8
Preparation of Pharmaceutical Formulations H–J

Pharmaceutical formulations H–J were prepared using the method of Example 7. The w/w % of the ingredients in the formulations is shown in Table 5 below.

TABLE 5

| Formulation Component | G (% w/w) | H (% w/w) | I (% w/w) | J (% w/w) |
|---|---|---|---|---|
| Isostearic Acid (874) | 15.00 | 15.00 | 15.00 | 18.00 |
| Imiquimod | 0.10 | 0.50 | 1.50 | 3.00 |
| Sorbitan Trioleate | 1.00 | 1.00 | 1.00 | 1.00 |
| Propylene Glycol | 5.00 | 5.00 | 5.00 | 5.00 |
| Sorbic Acid | 0.15 | 0.15 | 0.15 | 0.15 |
| Methylparaben | 0.20 | 0.20 | 0.20 | 0.20 |
| Purified Water | 75.00 | 74.60 | 73.60 | 69.10 |
| Edetate Disodium | 0.05 | 0.05 | 0.05 | 0.05 |
| Polaxamer 188 | 2.50 | 2.50 | 2.50 | 2.50 |
| Carbomer 974 | 1.00 | 1.00 | 1.00 | 1.00 |
| Sodium Hydroxide | qs | qs | qs | Os |
| Total % w/w | 100 | 100 | 100 | 100 |

Accordingly, from the foregoing discussion, it will appreciated that the imidazoquinoline amines, imidazopyridine amines, 6,7-fused cycloalkylimidazopyridine amines, and 1,2-bridged imidazoquinoline amines of the present invention can be beneficial for treating mucosal associated conditions including cervical dysplasias. In addition, the disclosed pharmaceutical formulations can be particularly advantageous for topical application of an IRM to a mucosal surface.

From the foregoing detailed description and examples, it will be evident that modifications and variations can be made in the compounds, formulations, devices, systems, and methods disclosed herein. Other embodiments will be apparent to those skilled in the art. It is intended that the specification and examples be considered as exemplary only.

What is claimed is:

1. A system for treating a condition associated with a mucosal surface, the system comprising a pharmaceutical formulation and an applicator device for applying the formulation to the mucosal surface, wherein the pharmaceutical formulation comprises:
    (a) an immune response modifier compound selected from the group consisting of imidazoquinoline amines, imidazopyridine amines, 6,7-fused cycloalkylimidazopyridine amines, 1,2-bridged imidazoquinoline amines, and pharmaceutically acceptable salts thereof;
    (b) a fatty acid; and
    (c) a preservative system comprising propylene glycol.

2. The system of claim 1 wherein the compound is 1-(2-methylpropyl)-1H-imidazo[4,5-c]-quinolin-4-amine or a pharmaceutically acceptable salt thereof.

3. The system of claim 1 wherein the compound is 4-amino-α,α-dimethyl-2-ethoxymethyl-1H-imidazo[4,5-c]quinoline-1-ethanol or a pharmaceutically acceptable salt thereof.

4. The system of claim 1 system of the applicator device is pre-filled with a therapeutically effective amount of the compound.

5. The system of claim 1 wherein the formulation is contained in a container separate from the device.

6. The system of claim 1 further comprising measuring marks on the applicator device for assisting a user in determining the amount of the formulation in the applicator device.

7. A system for treating a condition associated with a mucosal surface, the system comprising:
    (a) an immune response modifier compound selected from the group consisting of imidazoquinoline amines, imidazopyridine amines, 6,7-fused cycloalkylimidazopyridine amines, 1,2-bridged imidazoquinoline amines, and pharmaceutically acceptable salts thereof; and
    (b) an applicator device for applying the compound to the mucosal surface, wherein the compound is contained in a container separate from the device.

8. A system for treating a condition associated with a mucosal surface, the system comprising:
    (a) an immune response modifier compound selected from the group consisting of imidazoquinoline amines, imidazopyridine amines, 6,7-fused cycloalkylimidazopyridine amines, 1,2-bridged imidazoquinoline amines, and pharmaceutically acceptable salts thereof; and
    (b) an applicator device for applying the compound to the mucosal surface that comprises measuring marks on the applicator device for assisting a user in determining the amount of compound in the applicator device.

9. A system for treating a condition associated with a mucosal surface, the system comprising:
    (a) an immune response modifier compound selected from the group consisting of imidazoquinoline amines, imidazopyridine amines, 6,7-fused cycloalkylimidazopyridine amines, 1,2-bridged imidazoquinoline amines, and pharmaceutically acceptable salts thereof; and
    (b) an applicator device for applying the compound to the mucosal surface that comprises a hollow tube comprising a distal delivery end and a proximal end; and a piston slidably received within the tube.

10. The system of claim 9, further comprising a member configured to cause movement of the piston toward the distal end.

11. The system of claim 10, wherein the device is configured to limit retraction movement of the member toward the proximal end when the piston is located adjacent to the distal end.

12. The system of claim 10, wherein the piston is removably coupled to the member.

13. The system of claim 10, wherein the member is slidably received in the hollow tube.

14. The system of claim 9, further comprising a stop limiting retraction movement of the piston toward the proximal end.

15. The system of claim 9, wherein the piston comprises a portion extending from the distal end when the piston is positioned at its farthest location away from the proximal end.

16. The system of claim 9, wherein the distal end is tapered on its outer surface.

17. The system of claim 10, wherein the member has a length shorter than the distance between the proximal end and the piston when the piston is positioned at its furthest location away from the proximal end.

18. The system of claim 7 wherein the compound is 1-(2-methylpropyl)-1H-imidazo[4,5-c]-quinolin-4-amine or a pharmaceutically acceptable salt thereof.

19. The system of claim 7 wherein the compound is 4-amino-α,α-dimethyl-2-ethoxymethyl-1H-imidazo[4,5-c]quinoline-1-ethanol or a pharmaceutically acceptable salt thereof.

20. The system of claim 8 wherein the compound is 1-(2-methylpropyl)-1H-imidazo[4,5-c]-quinolin-4-amine or a pharmaceutically acceptable salt thereof.

21. The system of claim 8 wherein the compound is 4-amino-α,α-dimethyl-2-ethoxymethyl-1H-imidazo[4,5-c]quinoline-1-ethanol or a pharmaceutically acceptable salt thereof.

22. The system of claim 9 wherein the compound is 1-(2-methylpropyl)-1H-imidazo[4,5-c]-quinolin-4-amine or a pharmaceutically acceptable salt thereof.

23. The system of claim 9 wherein the compound is 4-amino-α,α-dimethyl-2-ethoxymethyl-1H-imidazo[4,5-c]quinoline-1-ethanol or a pharmaceutically acceptable salt thereof.

24. A system for treating a condition associated with a mucosal surface, the system comprising a pharmaceutical formulation and an applicator device for applying the formulation to the mucosal surface, wherein the pharmaceutical formulation comprises:

(a) an immune response modifier compound selected from the group consisting of imidazoquinoline amines, imidazopyridine amines, 6,7-fused cycloalkylimidazopyridine amines, imidazonaphthyridine amines, oxazoloquinoline amines, thiazoloquinoline amines, 1,2-bridged imidazoquinoline amines, and pharmaceutically acceptable salts thereof;

(b) a fatty acid; and (c) a preservative system comprising propylene glycol.

25. The system of claim 24 wherein the compound is an imidazonaphthyridine amine, or a pharmaceutically acceptable salt thereof.

26. The system of claim 24 wherein the compound is an oxazoloquinoline amine, or a pharmaceutically acceptable salt thereof.

27. The system of claim 24 wherein the compound is an thiazoloquinoline amine, or a pharmaceutically acceptable salt thereof.

28. A system for treating a condition associated with a mucosal surface, the system comprising:

(a) an immune response modifier compound selected from the group consisting of imidazoquinoline amines, imidazopyridine amines, 6,7-fused cycloalkylimidazopyridine amines, imidazonaphthyridine amines, oxazoloquinoline amines, thiazoloquinoline amines, 1,2-bridged imidazoquinoline amines, and pharmaceutically acceptable salts thereof; and (b) an applicator device for applying the compound to the mucosal surface, wherein the compound is contained in a container separate from the device.

29. The system of claim 28 wherein the compound is an imidazonaphthyridine amine, or a pharmaceutically acceptable salt thereof.

30. The system of claim 28 wherein the compound is an oxazoloquinoline amine, or a pharmaceutically acceptable salt thereof.

31. The system of claim 28 wherein the compound is an thiazoloquinoline amine, or a pharmaceutically acceptable salt thereof.

32. A system for treating a condition associated with a mucosal surface, the system comprising:

(a) an immune response modifier compound selected from the group consisting of imidazoquinoline amines, imidazopyridine amines, 6,7-fused cycloalkylimidazopyridine amines, imidazonaphthyridine amines, oxazoloquinoline amines thiazoloquinoline amines, 1,2-bridged imidazoquinoline amines, and pharmaceutically acceptable salts thereof; and (b) an applicator device for applying the compound to the mucosal surface that comprises measuring marks on the applicator device for assisting a user in determining the amount of compound in the applicator device.

33. The system of claim 32 wherein the compound is an imidazonaphthyridine amine, or a pharmaceutically acceptable salt thereof.

34. The system of claim 32 wherein the compound is an oxazoloquinoline amine, or a pharmaceutically acceptable salt thereof.

35. The system of claim 32 wherein the compound is an thiazoloquinoline amine, or a pharmaceutically acceptable salt thereof.

36. A system for treating a condition associated with a mucosal surface, the system comprising:

(a) an immune response modifier compound selected from the group consisting of imidazoquinoline amines, imidazopyridine amines, 6,7-fused cycloalkylimidazopyridine amines, imidazonaphthyridine amines, oxazoloquinoline amines, thiazoloquinoline amines, 1,2-bridged imidazoquinoline amines, and pharmaceutically acceptable salts thereof; and (b) an applicator device for applying the compound to the mucosal surface that comprises a hollow tube comprising a distal delivery end and a proximal end; and a piston slidably received within the tube.

37. The system of claim 36 wherein the compound is an imidazonaphthyridine amine, or a pharmaceutically acceptable salt thereof.

38. The system of claim 36 wherein the compound is an oxazoloquinoline amine, or a pharmaceutically acceptable salt thereof.

39. The system of claim 36, wherein the compound is an thiazoloquinoline amine, or a pharmaceutically acceptable salt thereof.

* * * * *

UNITED STATES PATENT AND TRADEMARK OFFICE
CERTIFICATE OF CORRECTION

PATENT NO. : 6,706,728 B2
DATED : March 16, 2004
INVENTOR(S) : Hedenstrom, John C.

It is certified that error appears in the above-identified patent and that said Letters Patent is hereby corrected as shown below:

<u>Title page,</u>
Item [56], References Cited, OTHER PUBLICATIONS, "Testerman, et al" reference please delete "inudction" and insert thereof -- induction --; and
"Buck, et al" reference, please delete "imiqumod" and insert in place thereof -- imiquimod --.

<u>Column 31,</u>
Line 54, please delete "The system of claim 1 system of" and insert in place thereof -- The system of claim 1 wherein --.

Signed and Sealed this

Thirteenth Day of July, 2004

JON W. DUDAS
*Acting Director of the United States Patent and Trademark Office*